United States Patent
Cragg et al.

(10) Patent No.: US 8,287,594 B2
(45) Date of Patent: Oct. 16, 2012

(54) KNEE JOINT PROSTHESIS AND HYALURONATE COMPOSITIONS FOR TREATMENT OF OSTEOARTHRITIS

(75) Inventors: Andrew H. Cragg, Edina, MN (US); Richard J. Greff, St. Pete Beach, FL (US); George Wallace, Coto de Caza, CA (US); Robert J. Socci, Jr., San Juan Capistrano, CA (US); Jonathan Kagan, Hopkins, MN (US); Rodolfo C. Quijano, Laguna Hills, CA (US); Hosheng Tu, Newport Beach, CA (US)

(73) Assignee: Intersect Partners, LLC, Lake Forest, CA (US)

( * ) Notice: Subject to any disclaimer, the term of this patent is extended or adjusted under 35 U.S.C. 154(b) by 0 days.

(21) Appl. No.: 12/949,204

(22) Filed: Nov. 18, 2010

(65) Prior Publication Data
US 2011/0172768 A1    Jul. 14, 2011

Related U.S. Application Data

(63) Continuation of application No. 11/974,538, filed on Oct. 15, 2007, now abandoned.

(60) Provisional application No. 60/852,885, filed on Oct. 19, 2006, provisional application No. 60/919,305, filed on Mar. 20, 2007.

(51) Int. Cl.
*A61F 2/08* (2006.01)
(52) U.S. Cl. ................................... 623/14.12
(58) Field of Classification Search .............. 623/14.12, 623/16.11, 17.11–17.16, 18.12, 18.11, 20.14
See application file for complete search history.

(56) References Cited

U.S. PATENT DOCUMENTS

| | | | |
|---|---|---|---|
| 3,140,712 A * | 7/1964 | Hunter | 623/18.12 |
| 4,024,588 A * | 5/1977 | Janssen et al. | 623/18.12 |
| 4,269,826 A * | 5/1981 | Zimmermann et al. | 424/1.17 |
| 4,344,193 A * | 8/1982 | Kenny | 623/14.12 |
| 4,502,161 A * | 3/1985 | Wall | 623/14.12 |
| 4,693,722 A | 9/1987 | Wall | |
| 4,795,768 A | 1/1989 | Ancker et al. | |
| 4,827,945 A * | 5/1989 | Groman et al. | 424/9.32 |
| 4,919,667 A * | 4/1990 | Richmond | 623/14.12 |
| 5,067,964 A * | 11/1991 | Richmond et al. | 623/14.12 |
| 5,092,894 A * | 3/1992 | Kenny | 128/898 |
| 5,158,574 A * | 10/1992 | Stone | 264/108 |
| 5,171,322 A | 12/1992 | Kenny | |
| 5,306,311 A * | 4/1994 | Stone et al. | 623/14.12 |
| 5,344,459 A * | 9/1994 | Swartz | 623/14.12 |
| 5,358,525 A * | 10/1994 | Fox et al. | 623/14.12 |
| 5,595,563 A * | 1/1997 | Moisdon | 600/12 |
| 5,651,989 A * | 7/1997 | Volkonsky et al. | 424/490 |
| 5,681,353 A * | 10/1997 | Li et al. | 623/14.12 |

(Continued)

OTHER PUBLICATIONS

International Search Report for Application No. PCT/US2008/080038 dated Apr. 28, 2009.

*Primary Examiner* — Alvin J. Stewart
(74) *Attorney, Agent, or Firm* — Knobbe, Martens, Olson & Bear, LLP

(57) ABSTRACT

A medical device and methods to relieve joint pain and adapted for knee joint repair, replacement and augmentation. The invention discloses joint lubricant, particularly hyaluronate compositions and methods for treatment of osteoarthritis.

5 Claims, 17 Drawing Sheets

U.S. PATENT DOCUMENTS

| | | | |
|---|---|---|---|
| 5,804,303 A | 9/1998 | Lorenz et al. | |
| 5,879,386 A * | 3/1999 | Jore | 623/16.11 |
| 6,005,161 A | 12/1999 | Brekke et al. | |
| 6,046,379 A | 4/2000 | Stone et al. | |
| 6,110,210 A * | 8/2000 | Norton et al. | 623/17.16 |
| 6,132,468 A | 10/2000 | Mansmann | |
| 6,176,880 B1 | 1/2001 | Plouhar et al. | |
| 6,206,927 B1 * | 3/2001 | Fell et al. | 623/20.29 |
| 6,292,680 B1 * | 9/2001 | Somogyi et al. | 600/407 |
| 6,352,558 B1 | 3/2002 | Spector | |
| 6,482,436 B1 * | 11/2002 | Volkonsky et al. | 424/489 |
| 6,530,956 B1 | 3/2003 | Mansmann | |
| 6,558,421 B1 | 5/2003 | Fell et al. | |
| 6,599,321 B2 * | 7/2003 | Hyde, Jr. | 623/18.12 |
| 6,629,997 B2 | 10/2003 | Mansmann | |
| 6,679,914 B1 * | 1/2004 | Gabbay | 623/14.12 |
| 6,690,617 B2 | 2/2004 | Cribbs | |
| 6,699,252 B2 * | 3/2004 | Farr et al. | 606/79 |
| 6,793,676 B2 * | 9/2004 | Plouhar et al. | 623/14.12 |
| 6,800,298 B1 | 10/2004 | Burdick et al. | |
| 6,815,063 B1 * | 11/2004 | Mayes | 428/402 |
| 6,893,463 B2 * | 5/2005 | Fell et al. | 623/14.12 |
| 6,899,667 B2 * | 5/2005 | Becker et al. | 600/9 |
| 6,905,514 B2 | 6/2005 | Carignan et al. | |
| 6,923,831 B2 * | 8/2005 | Fell et al. | 623/14.12 |
| 6,994,730 B2 | 2/2006 | Posner | |
| 7,004,971 B2 * | 2/2006 | Serhan et al. | 623/17.16 |
| 7,124,762 B2 * | 10/2006 | Carter et al. | 128/898 |
| 7,163,563 B2 * | 1/2007 | Schwartz et al. | 623/23.76 |
| 7,179,295 B2 * | 2/2007 | Kovacevic | 623/17.15 |
| 7,195,645 B2 * | 3/2007 | Disilvestro et al. | 623/18.11 |
| 7,244,273 B2 * | 7/2007 | Pedersen et al. | 623/14.12 |
| 7,291,169 B2 * | 11/2007 | Hodorek | 623/14.12 |
| 7,297,161 B2 * | 11/2007 | Fell | 623/14.12 |
| 7,462,199 B2 * | 12/2008 | Justin et al. | 623/20.34 |
| 7,476,250 B1 * | 1/2009 | Mansmann | 623/14.12 |
| 7,534,263 B2 * | 5/2009 | Burdulis et al. | 623/14.12 |
| 7,594,922 B1 * | 9/2009 | Goble et al. | 606/213 |
| 7,611,653 B1 * | 11/2009 | Elsner et al. | 264/255 |
| 7,618,451 B2 * | 11/2009 | Berez et al. | 623/14.12 |
| 7,717,956 B2 * | 5/2010 | Lang | 623/14.12 |
| 7,758,643 B2 * | 7/2010 | Stone et al. | 623/14.12 |
| 7,799,077 B2 * | 9/2010 | Lang et al. | 623/14.12 |
| 7,811,328 B2 * | 10/2010 | Molz et al. | 623/17.16 |
| 7,819,918 B2 * | 10/2010 | Malaviya et al. | 623/14.12 |
| 7,819,919 B2 * | 10/2010 | Fell | 623/14.12 |
| 7,879,105 B2 * | 2/2011 | Schmieding et al. | 623/19.11 |
| 8,077,950 B2 * | 12/2011 | Tsougarakis et al. | 382/128 |
| 8,080,059 B2 * | 12/2011 | Fell | 623/14.12 |
| 8,092,530 B2 * | 1/2012 | Strzepa et al. | 623/14.12 |
| 8,114,156 B2 * | 2/2012 | Hatch | 623/14.12 |
| 8,128,697 B2 * | 3/2012 | Fell et al. | 623/14.12 |
| 2001/0002446 A1 * | 5/2001 | Plouhar et al. | 623/14.12 |
| 2002/0022884 A1 * | 2/2002 | Mansmann | 623/14.12 |
| 2002/0032484 A1 * | 3/2002 | Hyde, Jr. | 623/18.12 |
| 2002/0127264 A1 | 9/2002 | Felt et al. | |
| 2003/0060882 A1 * | 3/2003 | Fell et al. | 623/14.12 |
| 2003/0060883 A1 * | 3/2003 | Fell et al. | 623/14.12 |
| 2003/0187510 A1 | 10/2003 | Hyde | 623/18.12 |
| 2003/0195633 A1 * | 10/2003 | Hyde, Jr. | 623/18.12 |
| 2003/0236572 A1 * | 12/2003 | Bertram, III | 623/18.12 |
| 2004/0039454 A1 * | 2/2004 | Herr et al. | 623/39 |
| 2004/0059423 A1 * | 3/2004 | Barnes et al. | 623/18.12 |
| 2004/0133275 A1 | 7/2004 | Mansmann | |
| 2004/0136905 A1 * | 7/2004 | Kent et al. | 424/1.11 |
| 2004/0139975 A1 * | 7/2004 | Nelson et al. | 128/848 |
| 2004/0195727 A1 | 10/2004 | Stoy | |
| 2004/0199249 A1 * | 10/2004 | Fell | 623/14.12 |
| 2004/0236424 A1 * | 11/2004 | Berez et al. | 623/14.12 |
| 2004/0267371 A1 | 12/2004 | Hayes, Jr. et al. | |
| 2005/0027307 A1 | 2/2005 | Schwartz et al. | |
| 2005/0033424 A1 * | 2/2005 | Fell | 623/14.12 |
| 2005/0043808 A1 | 2/2005 | Felt et al. | |
| 2005/0113840 A1 | 5/2005 | Metzger et al. | |
| 2005/0137708 A1 | 6/2005 | Clark | |
| 2005/0178396 A1 | 8/2005 | Hunter et al. | |
| 2005/0209703 A1 * | 9/2005 | Fell | 623/20.33 |
| 2005/0234549 A1 | 10/2005 | Kladakis et al. | |
| 2005/0234555 A1 * | 10/2005 | Sutton et al. | 623/17.15 |
| 2005/0267584 A1 * | 12/2005 | Burdulis et al. | 623/20.19 |
| 2006/0004459 A1 * | 1/2006 | Hazebrouck et al. | 623/18.12 |
| 2006/0064169 A1 | 3/2006 | Ferree | |
| 2006/0069447 A1 * | 3/2006 | DiSilvestro et al. | 623/23.16 |
| 2006/0079897 A1 * | 4/2006 | Harrison et al. | 606/61 |
| 2006/0136062 A1 * | 6/2006 | DiNello et al. | 623/17.14 |
| 2006/0155380 A1 | 7/2006 | Clemow et al. | |
| 2006/0178497 A1 | 8/2006 | Gevaert et al. | |
| 2006/0235517 A1 * | 10/2006 | Hodorek | 623/14.12 |
| 2006/0247782 A1 * | 11/2006 | Molz et al. | 623/17.16 |
| 2006/0282168 A1 * | 12/2006 | Sherman et al. | 623/18.12 |
| 2007/0004994 A1 * | 1/2007 | Sherman | 602/26 |
| 2007/0100457 A1 * | 5/2007 | Hyde, Jr. | 623/18.12 |
| 2007/0100462 A1 * | 5/2007 | Lang et al. | 623/20.29 |
| 2007/0179607 A1 | 8/2007 | Hodorek et al. | |
| 2008/0097606 A1 * | 4/2008 | Cragg et al. | 623/14.12 |
| 2008/0140094 A1 | 6/2008 | Schwartz et al. | |
| 2008/0154371 A1 * | 6/2008 | Fell et al. | 623/14.12 |
| 2008/0306324 A1 * | 12/2008 | Bonutti et al. | 600/12 |
| 2009/0118830 A1 * | 5/2009 | Fell | 623/14.12 |
| 2009/0132047 A1 * | 5/2009 | Mansmann et al. | 623/14.12 |
| 2010/0036493 A1 * | 2/2010 | Simon | 623/14.12 |
| 2010/0145464 A1 * | 6/2010 | Sidhom | 623/18.12 |
| 2011/0015748 A1 * | 1/2011 | Molz et al. | 623/17.16 |
| 2011/0093073 A1 * | 4/2011 | Gatt et al. | 623/14.12 |
| 2011/0172768 A1 * | 7/2011 | Cragg et al. | 623/14.12 |
| 2012/0004725 A1 * | 1/2012 | Shterling et al. | 623/14.12 |
| 2012/0022649 A1 * | 1/2012 | Robinson et al. | 623/14.12 |

* cited by examiner

POSITIONING OF INSERTED MENSICAL LINER

ATTACHMENT OF A MENISCAL LINER USING SUTURES

ATTACHMENT OF A MENISCAL LINER USING SUTURES

INSERTION OF MENISCAL LINER WITHOUT
USE OF AN INSERTION CANNULA

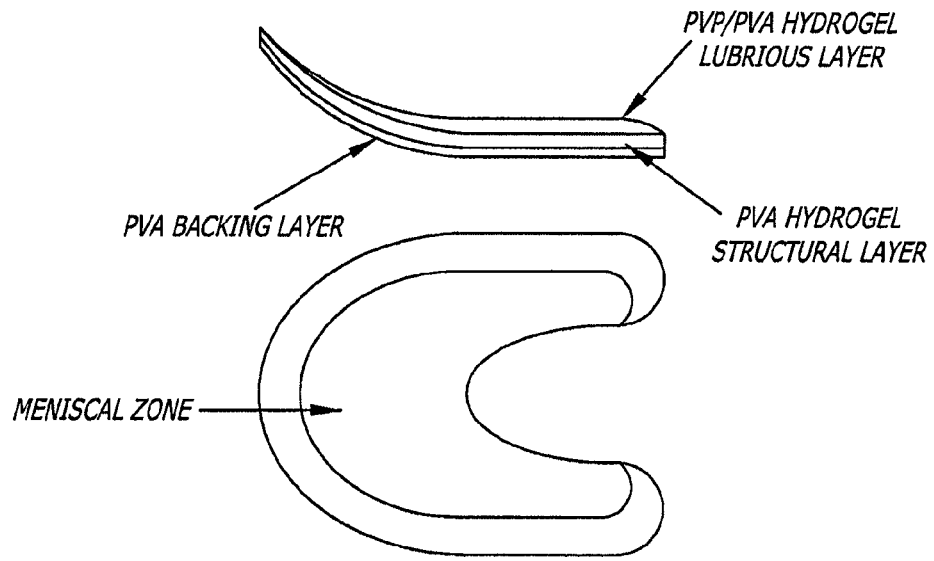
FIG. 7A EXEMPLARY MENISCAL LINER
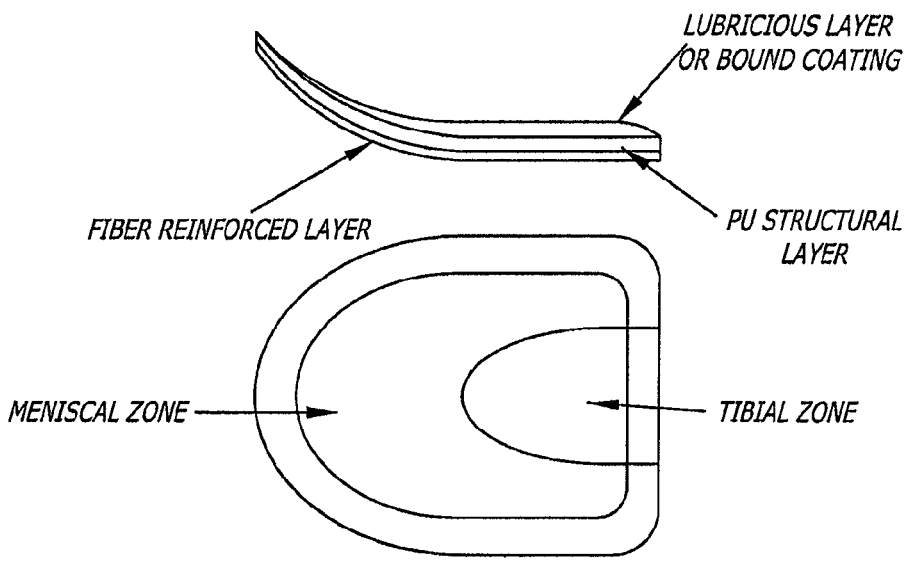
FIG. 7B EXEMPLARY COMBINED MENISCAL/TIBIAL LINER

CONDYLAR COVER

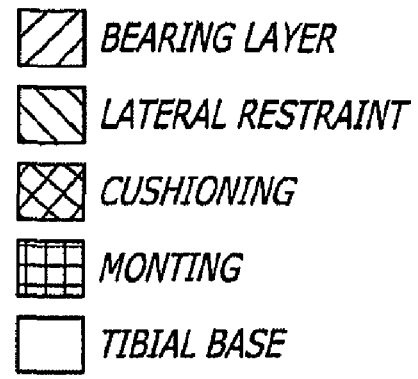
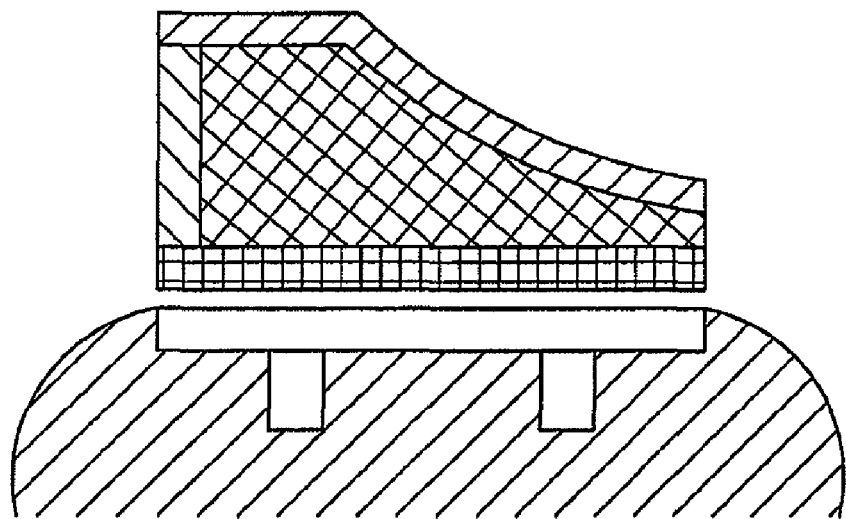
FIG. 15

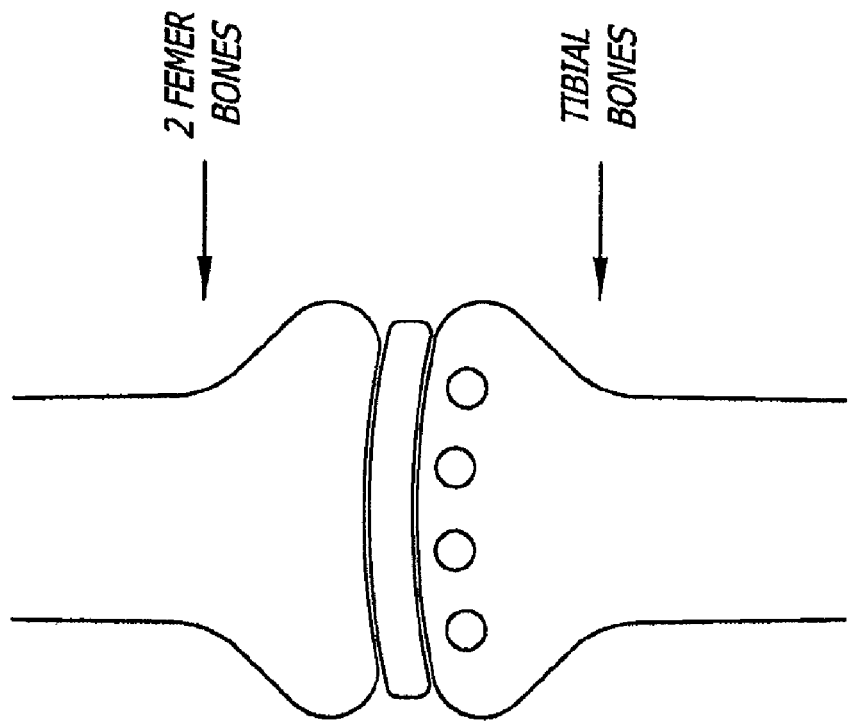
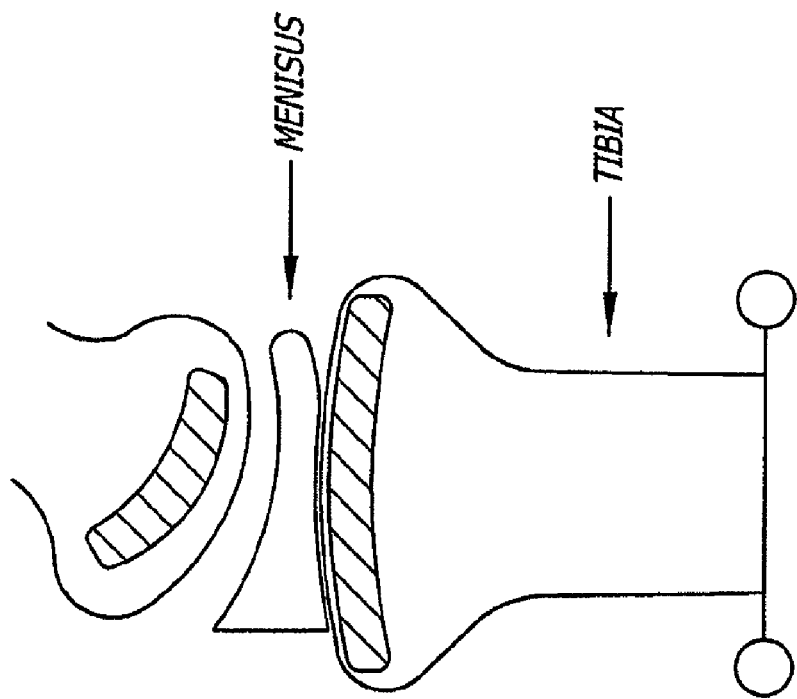
FIG. 20

KNEE JOINT PROSTHESIS AND HYALURONATE COMPOSITIONS FOR TREATMENT OF OSTEOARTHRITIS

CROSS-REFERENCE TO RELATED APPLICATIONS

This application is a continuation of U.S. patent application Ser. No. 11/974,538 filed Oct. 15, 2007, now abandoned which claims the priority benefits of U.S. Provisional Application No. 60/852,885 filed Oct. 19, 2006 and U.S. Provisional Application No. 60/919,305 filed Mar. 20, 2007.

FIELD OF THE INVENTION

The present invention is generally related to therapies for treating a joint or other body parts of a patient. More particularly, the present invention is related to a medical device, hyaluronic compositions, and methods for treatment of osteoarthritis or relieving joint pain adapted for knee joint repair, replacement and augmentation.

BACKGROUND OF THE INVENTION

The knee is very complex and, includes many components with many functions. The knee problems may be related to meniscus, pain, cartilage, shock absorption, synovial fluids, articular cartilage, ligaments/tendons and/or preserving normal biomechanics. Available therapy currently includes chronic synovial lubrication, acute synovial lubrication, meniscal protection, meniscal augmentation, partial meniscal replacement, total meniscal replacement, and partial or total knee prosthesis.

The menisci are crescents roughly triangular in cross section, covering one-half to two thirds of the articular surface of the corresponding tibial plateau. The outer rims of the menisci are convex and attached to the knee joint capsule. The inner edges are concave, thin and free. The anatomy of menisci and knee joints can be found in any anatomy book, for example, Gray's Anatomy of the Human Body, $20^{th}$ edition, New York, Bartleby.com 2000.

The menisci extend the superior tibial surface, improving its congruency with the femoral condyles. Both menisci are fibrocartilaginous and wedge shaped in the coronal plane. The medial meniscus is crescent shaped, and the lateral meniscus is more circular. The superior portions of the menisci are concave, enabling effective articulation with their respective convex condyles, whereas the inferior surfaces are flat to conform to the tibial plateaus. Anterior and posterior meniscal horns attach to the intercondylar eminence of the tibial plateau. The coronary ligaments provide peripheral attachments between the tibial plateau and the perimeter of both menisci. The medial meniscus is also attached to the medial collateral ligament, which limits its mobility. The lateral meniscus is connected to the femur via the anterior and posterior meniscofemoral ligaments, which can tension its posterior horn anteriorly and medially with increasing knee flexion. The transverse ligament provides a connection between the anterior aspects of both menisci. The increased stability provided by the ligamentous attachments prevents the menisci from being extruded out of the joint during compression.

The knee joint is innervated by the posterior articular branch of the posterior tibial nerve and the terminal branches of the obturator and femoral nerves. Nerve fibers generally penetrate the joint capsule, along with the vascular supply and service the substance of the menisci.

Vascular supply is crucial to meniscal healing. The medial, lateral, and middle geniculate arteries, which branch off the popliteal artery, provide the major vascularization to the inferior and superior aspects of each meniscus. Only 10% to 30% of the peripheral medial meniscus border and 10% to 25% of the lateral meniscus border receive direct blood supply. The remaining portion of each meniscus receives nourishment only from the synovial fluid via diffusion or mechanical pumping. The latter mechanism derives from intermittent compression of the tissue during function. Mechanical pumping through joint flexion may be essential for continued nutrition.

The major meniscal functions are to distribute stress across the knee during weight bearing, provide shock absorption, serve as secondary joint stabilizers, provide articular cartilage nutrition and lubrication, facilitate joint gliding, prevent hyperextension, and protect the joint margins. During knee flexion, the femoral condyles glide posteriorly on the tibial plateau in conjunction with tibial internal rotation. The lateral meniscus undergoes twice the anteroposterior translation of the medial meniscus during knee flexion.

Type I collagen fibers provide the primary meniscal structural scaffolding; this predominance of type I collagen is one of the major differences between the menisci and hyaline, or articular, cartilage, which is composed of predominantly type II collagen. Three collagen fiber layers are specifically arranged to convert compressive loads into circumferential or "hoop" stresses. In the superficial layer, the fibers travel radially, serving as "ties" that resist shearing or splitting. In the middle layer, the fibers run parallel or circumferentially to resist hoop stress during weight bearing. Lastly, there is a deep layer of collagen bundles that are aligned parallel to the periphery.

Osteoarthritis (OA, also known as degenerative arthritis or degenerative joint disease) is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis. The main symptom is chronic pain, causing loss of mobility and often stiffness. "Pain" is generally described as a sharp ache, or a burning sensation in the associated muscles and tendons. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used throughout the day, thus distinguishing it from rheumatoid arthritis.

The primary osteoarthritis is caused by aging. As a person ages, the water content of the cartilage decreases, and the protein composition in it degenerates, thus degenerating the cartilage through repetitive use or misuse. Inflammation can also occur, and stimulate new bone outgrowths, called "spurs" (osteophyte), to form around the joints. Sufferers find their every movement so painful and debilitating that it can also affect them emotionally and psychologically.

The secondary osteoarthritis is caused by one or more of the following conditions or diseases: (1) congenital disorders, such as congenital hip luxation; (2) cracking joints; (3) diabetes; (4) Inflammatory diseases, such as Perthes' disease, and all chronic forms of arthritis (e.g. costochondritis, gout, and rheumatoid arthritis); (5) injury to joints; (6) ligamentous deterioration of instability; (7) hormonal disorders; (8) obesity; (9) osteopetrosis; (10) sports injury; and (11) surgery to the joint structures.

Heatley reported that repair of incisions in the central part of the meniscus on rabbits has demonstrated after surgical excision of the peripheral rim (J bone Joint Surg 1980; 62-B: 397-402). Healing took place via a highly cellular but relatively avascular fibrous tissue stroma which proliferated from the synovial margin and invaded along the cut edge of the meniscus. Suturing facilitated this healing process by providing stability and possibly by supplying bridges for synovial cells to migrate onto the meniscus.

U.S. Pat. No. 4,344,193 issued on Aug. 17, 1982, entire contents of which are incorporated herein by reference, discloses a meniscus prosthetic device for a human knee joint so that the articulating cartilage in the knee totally remains intact. The prosthesis device translates between the articulating cartilages during normal knee movement. Insertion of the prosthetic device is accomplished by applying force on the ends of the device, thereby elastically spreading them, and placing the device between the tibial articulating cartilage and one of the femoral condyles. Prominences on the ends of the device may superiorly extend into the space defined by the femoral condyles, thereby securing the device in place.

U.S. Pat. No. 4,502,161 issued on Mar. 5, 1985, entire contents of which are incorporated herein by reference, discloses a prosthetic meniscus that is located between the natural articular surfaces of the bones of a joint. The prosthetic meniscus includes a body portion formed of a resilient material and further defines an extra-articular extension which is attached to the surface of the bone outside the joint. A reinforcing fabric or mesh is embedded in the resilient material to give the meniscus strength and shape.

U.S. Pat. No. 4,693,722 issued on Sep. 15, 1987, entire contents of which are incorporated herein by reference, discloses a prosthetic device for a temporomandibular joint comprising a prosthetic condyle and a prosthetic meniscus. The prosthetic condyle comprises two plates that are clamped about the ramus of the mandible wherein one of the plates extends upwardly into a convex surface thereby forming the condyle. The prosthetic meniscus comprising a resilient insert which is inserted into the joint capsule and has a reinforcing mesh embedded therein, and an extension for attaching the meniscus to the temporal bone.

U.S. Pat. No. 4,795,468 issued on Jan. 3, 1989, entire contents of which are incorporated herein by reference, discloses a mechanism and method for locking or securing a bearing insert to the base of a prosthetic implant. The prosthetic implant is for replacement of a portion of natural bone at the point of articulation. The implant includes a locking mechanism which enables the bearing insert to be removably secured to the base support. The locking mechanism includes a resilient locking clip which is predisposed on one side of either the bearing insert or the base support such that when the bearing insert and base support are assembled together, the clip extends between both the insert and the support to secure the two components together. To insert and/or remove the bearing insert from the support, the clip is caused to substantially fully recede into the component in which it is predisposed.

U.S. Pat. No. 4,919,667 issued on Apr. 24, 1990, entire contents of which are incorporated herein by reference, discloses a soft tissue implant in the form of a meniscus cartilage replacement for a patient. Appropriately shaped top and bottom layers sandwich therebetween at least one intermediate felted layer. A resilient bonding material coats the layers and holds same in a laminated condition. The top layer is contoured, to provide a wedge shaped cross section and a contoured three dimensional shape. A fabric member is bonded to the thickened edge of the laminant and is porous to invite ingrowth of patient tissue to anchor the implant eventually in place.

U.S. Pat. No. 5,067,964 issued on Nov. 26, 1991, entire contents of which are incorporated herein by reference, discloses an articular cartilage repair piece to substitute for a cut-out piece of damaged articular cartilage on a bone in an articulated joint. The repair piece includes a backing layer of non-woven, felted fibrous material which is conformable to flat and curved surfaces.

U.S. Pat. No. 5,092,894 issued on Mar. 3, 1992, entire contents of which are incorporated herein by reference, discloses a meniscus prosthetic device replacing natural components of a condylar joint. The body of the device is of biocompatible, deformable, flexible and resilient material for bearing compressive loads and for translating the loads to tensile stress. The tail of the device is also biocompatible material and extends as a continuation of the body from a first end to a second end of the body. The tail provides a continuous loop circuit for the propagation of hoop tensile stresses from the body, and provides stabilization of the knee joint and proprioceptive feedback. The prosthesis is implanted in a human knee in a position to take the place of a naturally occurring meniscus between the femoral condyle and the corresponding tibia, and the tail is placed into contact with bone associated with the knee.

U.S. Pat. No. 5,158,574 issued on Oct. 27, 1992, entire contents of which are incorporated herein by reference, discloses a prosthetic meniscus implanted in a human knee where it can act as a scaffold for regrowth of native meniscal tissues. The meniscus comprises a dry, porous, matrix of biocompatible and bioresorbable fibers, at least a portion of which may be crosslinked. The fibers include natural polymers, analogs, or mixtures thereof. The matrix is adapted to have in vivo an outer surface contour substantially the same as that of a natural meniscus. With this configuration, the matrix establishes an at least partially bioresorbable scaffold adapted for ingrowth of meniscal fibrochondrocytes.

U.S. Pat. No. 5,344,459 issued on Sep. 6, 1994, entire contents of which are incorporated herein by reference, discloses a prosthetic device which is arthroscopically implantable into a joint. The device has a ring or a pair of rings sized and shaped to fit within the joint. The ring or rings are comprised of a polymeric substance and may contain one or more compartments which are inflatable or expandable with air, a liquid or a semi-solid, through an arthroscope coupling means.

U.S. Pat. No. 6,046,379 issued on Apr. 4, 2000, entire contents of which are incorporated herein by reference, discloses an article of manufacture comprising a substantially non-immunogenic knee meniscal xenograft for implantation into humans. The invention further provides methods for preparing a knee meniscal xenograft by removing at least a portion of a meniscus from a non-human animal to provide a xenograft; washing the xenograft in saline and alcohol; and subjecting the xenograft to at least one treatment selected from the group consisting of exposure to ultraviolet radiation, immersion in alcohol, ozonation, and freeze/thaw cycling.

U.S. Pat. No. 5,171,322 issued on Dec. 15, 1992, entire contents of which are incorporated herein by reference, discloses a meniscus prosthetic device including a body and a tail. The body is of biocompatible, deformable, flexible and resilient material for bearing compressive loads and for translating the loads to tensile stress. The tail is also biocompatible material and extends as a continuation of the body from a first end to a second end of the body. The tail provides a continuous loop circuit for the propagation of tensile (hoop) stresses from the body, and provides stabilization of the knee joint and proprioceptive feedback.

U.S. Pat. No. 5,807,303 issued on Sep. 15, 1998, entire contents of which are incorporated herein by reference, discloses a device for relieving synovial fluid pressure in a capsule surrounding a body joint including a valve for placement in the capsule surrounding the joint for regulating passage of synovial fluid from the capsule. The valve can include a valve housing defining a passage between an interior and exterior of the capsule and a valve member disposed within the valve housing for regulating synovial fluid pressure within the capsule by permitting synovial fluid to drain from the capsule when a predetermined synovial fluid pressure is exceeded. The valve housing can be secured to the capsule with inlet and outlet flanges disposed at opposite ends of the housing and, additionally, by use of openings formed in the outlet flange to allow passage of sutures and to promote integral tissue fixation over time.

U.S. Pat. No. 6,005,161 issued on Dec. 21, 1999, entire contents of which are incorporated herein by reference, discloses a biodegradable device for facilitating healing of structural voids in bone, cartilage as well as soft tissue in the most preferred form including a porous macrostructure made from a biodegradable polymer and a chemotactic ground substance in the form of an RGD attachment moiety of fibronectin formed as a porous microstructure. For repair of articular cartilage, harvested precursor cells are secured to the biodegradable carrier which is shaped for press fitting into the articular cartilage lesion. In the most preferred form, biological modifiers such as transforming growth factor β and basic fibroblastic growth factor is incorporated in the biodegradable device to mediate cellular activity and regulate cellular functions.

U.S. Pat. No. 6,132,468 issued on Oct. 17, 2000, entire contents of which are incorporated herein by reference, discloses a flexible scaffold envelope which can be used to replace damaged cartilage. Designed for use in arthroscopic surgery, the envelope is sufficiently flexible to allow it to be rolled up or folded and inserted into a knee joint via a small skin incision. After the envelope is inserted into the joint, it is unfolded, positioned properly, and anchored and cemented to a bone surface. After anchoring, the envelope is filled via an inlet tube with a polymeric substance that will set and solidify at body temperature. During filling and setting, the surgeon can manipulate the exterior shape of the scaffold envelope, to ensure that the implant will have a proper final shape after the polymer has cured into fully solidified form.

U.S. Pat. No. 6,176,880, issued on Jan. 23, 2001, entire contents of which are incorporated herein by reference, discloses a reconstructive structure for a cartilaginous element having a plurality of superimposed layers of intestinal submucosa tissue compressed and secured together and shaped to provide a reconstructive structure having the anatomical shape of the cartilaginous element to be reconstructed is described. The method of forming the reconstructive structure includes superimposing the planar layers of the intestinal submucosa tissue, securing the layers to form a multi-layered structure and cutting the resulting multi-layered structure to the desired shape.

U.S. Pat. No. 6,352,558 issued on Mar. 5, 2002, entire contents of which are incorporated herein by reference, discloses a method of promoting regeneration of surface cartilage of a joint including the steps of forming punctures in a subchondral plate of an area of the joint to be treated, covering the puncture and the area to be treated with a chondrocyte-free patch made of a sheet of collagen membrane material without adding chondrocytes to the area to be treated, fixing the patch over the area to be treated, and allowing the area to be treated to regenerate cartilage without adding chondrocytes to the area to be treated.

U.S. Pat. No. 6,530,956 issued on Mar. 11, 2003, entire contents of which are incorporated herein by reference, discloses a load-sharing resorbable scaffold used to help transplanted chondrocytes or other cells generate new cartilage in a damaged joint such as a knee, hip, or shoulder. These scaffolds use two distinct matrix materials. One is a relatively stiff matrix material, designed to withstand and resist a compressive articulating load placed on the joint during the convalescent period, shortly after surgery. The second material comprises a more open and porous matrix, designed to promote maximal rapid generation of new cartilage. The scaffold would support the membrane with a degree of stiffness and resiliency that allows the membrane to mimic a healthy cartilage surface.

U.S. Pat. No. 6,629,997 issued on Oct. 7, 2003, entire contents of which are incorporated herein by reference, discloses a device for surgical implantation to replace damaged tissue in a joint (such as a meniscus in a knee) that is created from a hydrogel that is reinforced by a three-dimensional flexible fibrous mesh. In a meniscal implant, the mesh is exposed at one or more locations around the periphery, to provide anchoring attachments that can be sutured, pinned, or otherwise securely affixed to tissue that surrounds the implant. Articulating surfaces which will rub and slide against cartilage should be coated with a hydrogel layer that is completely smooth and nonabrasive, and made of a material that remains constantly wet.

U.S. Pat. No. 6,800,298 issued on Oct. 5, 2004, entire contents of which are incorporated herein by reference, discloses fluid compositions containing a dextran-based hydrogel with lipids that provides enhanced rheological and tribological properties of such a fluid. Phospholipids are particularly useful in dextran-based compositions for synovial fluid. One phospholipid that can be used advantageously in synovial fluid is dipalmitoyl phosphatidylcholine.

U.S. Pat. No. 6,893,463 issued on May 17, 2005, entire contents of which are incorporated herein by reference, discloses an implantable knee prosthesis including a two-piece body having a substantially elliptical shape in plane and including a first piece and a second piece. The first piece is a tibial piece including a tibial surface. The second piece is a femoral piece including a femoral surface. The first piece and the second piece are mutually slidably engagable and separable.

U.S. Pat. No. 6,905,514 issued on Jun. 14, 2005, entire contents of which are incorporated herein by reference, discloses a replacement device for resurfacing a joint surface of a femur. The custom replacement device is designed to substantially fit the trochlear groove surface of an individual femur. Thereby creating a "customized" replacement device for that individual femur and maintaining the original kinematics of the joint. The top surface is designed so as to maintain centrally directed tracking of the patella perpendicular to the plane established by the distal end of the femoral condyles and aligned with the center of the femoral head.

U.S. Pat. No. 6,960,617 issued on Nov. 1, 2005, entire contents of which are incorporated herein by reference, discloses hydrogels having improved elasticity and mechanical strength properties by subjecting a hydrogel formulation containing a strengthening agent to chemical or physical crosslinking conditions subsequent to initial gel formation. Superporous hydrogels having improved elasticity and mechanical strength properties are similarly obtained whenever the hydrogel formulation is provided with a foaming agent. Interpenetrating networks of polymer chains comprised of primary polymer and strengthening polymer are thereby formed. The primary polymer affords capillary-based water sorption properties while the strengthening polymer imparts significantly enhanced mechanical strength and elasticity to the hydrogel or superporous hydrogel. Suitable strengthening agents can be natural or synthetic polymers, polyelectrolytes, or neutral, hydrophilic polymers.

U.S. Pat. No. 6,994,730 issued on Feb. 7, 2006, entire contents of which are incorporated herein by reference, discloses a method for resurfacing a joint capsule having cartilage and meniscal surfaces such as a knee joint including resecting a central portion of the joint cartilage on one joint member such as the tibia while leaving a meniscal rim attached to the peripheral joint capsule. A cavity is then formed in the bone underlying the central portion of the joint surface such as the lateral tibial surface. A resurfacing implant is then coupled, by cementing for example, to the cavity. A soft prosthetic meniscal implant is then coupled to the remaining meniscal ring such as by suturing.

U.S. Pat. No. 7,008,635 issued on Mar. 7, 2006, entire contents of which are incorporated herein by reference, discloses hydrogels intended for orthopedic applications with a hydrogel formulation which has high strength, toughness, a suitable mechanical modulus and low equilibrium hydration. It may have controlled porosity or degradation time. It can be made to polymerize in situ with high adherence to target tissue or surfaces. A preferred formulation for forming such gels comprises 40 to 80% by weight of a low-molecular weight polar monomer and 30 to 10% of a hydrophilic macromeric crosslinker.

U.S. Pat. No. 7,060,074 issued on Jun. 13, 2006, entire contents of which are incorporated herein by reference, discloses instrumentation for use in minimally invasive unicompartmental knee replacement including a tibial cutting guide for establishing a planar surface along a tibial plateau and a tibial stylus having an anatomic contour for controlling the depth of the planar surface along the tibial plateau. The instrumentation further comprises a posterior resection block for preparing a posterior femoral resection, with a forward portion of the posterior resection block having a configuration corresponding to the configuration of a prosthetic femoral component. Instrumentation comprising a resection block and a resurfacing guide are provided for surgically preparing a femoral condyle to receive a prosthetic femoral component. The instrumentation further includes a resurfacing guide and a resurfacing instrument for resurfacing a femoral condyle to a controlled depth.

U.S. Application publication No. 2001/0043913 published on Nov. 12, 2001, entire contents of which are incorporated herein by reference, discloses a meniscal implant biomaterial made of a novel in situ produced macroporous biomedical polyurethane-amide material based on chain extended isocyanate terminated polyester prepolymer units, wherein the chain extension has been done with at least one dicarboxylic acid or a hydroxy-carboxylic acid.

U.S. Application publication No. 2002/0022884 published on Feb. 21, 2002, entire contents of which are incorporated herein by reference, discloses a device designed for surgical implantation to replace damaged tissue (such as a meniscus in a knee) having a hydrogel component reinforced by a three-dimensional mesh. The mesh component provides strength and structural support for the implant, which has at least one articulating surface, and at least one anchoring surface. In one embodiment, the mesh emerges from one or more selected locations around the peripheral rim of a meniscal implant, to provide anchoring attachments that can be sutured, pinned, clipped, or otherwise securely affixed to the fibrous capsule that surrounds the knee. This composite structure, with hydrogel layers surrounding an embedded mesh component, provides a joint-repair implant with improved anchoring, strength, and performance compared to implants of the prior art.

U.S. Application publication No. 2002/0127264 published on Sep. 12, 2002, entire contents of which are incorporated herein by reference, discloses a method and system for the creation or modification of the wear surface of orthopedic joints, involving the preparation and use of one or more partially or fully preformed and procured components, adapted for insertion and placement into the body and at the joint site. In a preferred embodiment, component(s) can be partially cured and generally formed ex vivo and further formed in vivo at the joint site to enhance conformance and improve long-term performance. In another embodiment, a preformed balloon or composite material can be inserted into the joint site and filled with a flowable biomaterial in situ to conform to the joint site.

U.S. Application publication No. 2004/0133275 published on Jul. 8, 2004, entire contents of which are incorporated herein by reference, discloses a permanent non-resorbable implant allowing surgical replacement of cartilage in articulating joints, using a hydro gel material (such as a synthetic polyacrylonitrile polymer) reinforced by a flexible fibrous matrix. Articulating hydrogel surface(s) are chemically treated to provide a negative electrical charge that emulates the negative charge of natural cartilage, and also can be treated with halogenating, cross-linking, or other chemical agents for greater strength.

U.S. Application publication No. 2004/0195727 published on Oct. 7, 2004, entire contents of which are incorporated herein by reference, discloses a method of making a lubricious polyacrylonitrile knee meniscus implant of a predetermined form and the resulting product.

U.S. Application publication No. 2004/0267371 published on Dec. 30, 2004, entire contents of which are incorporated herein by reference, discloses a prosthetic tibial component for a prosthetic total knee joint, that comprises two constructs, one being a metal base construct that engages the bone and the other being a polyethylene bearing construct that attaches to the metal base construct and articulates with a femoral prosthetic component on the opposing side of the joint. The metal base construct is composed of two different metals, one of which engages the bone surface and the other of which engages the polyethylene bearing construct. The first metal (i.e., the one that engages the bone surface) is selected so as to provide a superior bone-engaging face, while the second metal (i.e., the one that engages the polyethylene bearing construct) is selected so as to provide a superior polyethylene-engaging face.

U.S. Application publication No. 2005/0027307 published on Feb. 3, 2005, entire contents of which are incorporated herein by reference, discloses unitary surgical devices having a pair of fixating mechanisms connected to a base with suture, anchors or pre-formed holes in the base and further including extracellular matrix material either as part of the base or supported on the base. The extracellular matrix material serves as tissue regenerating material. The devices can be used either as an insert to be placed between and approximated to the inner surfaces of the tear or as an insert to replace a void in the meniscus left after a meniscectomy.

U.S. Application publication No. 2005/0033424 published on Feb. 10, 2005, entire contents of which are incorporated herein by reference, discloses a prosthesis for implantation into a knee joint compartment between a femoral condyle and its corresponding tibial plateau which reduces any excessive prosthesis motion. The prosthesis includes a hard body having a generally elliptical shape in plan and a pair of opposed surfaces including a bottom surface and an opposed top surface, the top surface having a first portion which is generally flat.

U.S. Application publication No. 2005/0043808 published on Feb. 24; 2005, entire contents of which are incorporated herein by reference, discloses a method and related composition and apparatus for repairing a tissue site. The method involves the use of a curable polyurethane biomaterial composition having a plurality of parts adapted to be mixed at the time of use in order to provide a flowable composition and to initiate cure. The flowable composition can be delivered using minimally invasive means to a tissue site and there fully cured provide a permanent and biocompatible prosthesis for repair of the tissue site. Further provided are a mold apparatus, e.g., in the form of a balloon or tubular cavity, for receiving a biomaterial composition, and a method for delivering and filling the mold apparatus with a curable composition in situ to provide a prosthesis for tissue repair.

U.S. Application publication No. 2005/0055101 published on Mar. 10, 2005, entire contents of which are incorporated herein by reference, discloses an endoprosthesis having improved self-lubrication mechanisms, the ability to filter the particles from the debris produced by the moving parts, and a new viscoelastic behavior under loading which reduce the transmitted forces. This has been achieved with the use of compressible materials and mechanisms between the fixed bearing and the tibial component, allowing the endoprosthesis to have compressibility under loading, which allows it also to receive or create chambers with an exit to the surface articulating with the femoral condyles.

U.S. Application publication No. 2005/0113840 published on May 26, 2005, entire contents of which are incorporated herein by reference, discloses various method and apparatuses used to perform a resection of a portion of the anatomy for preparation of the implants of a prosthetic. Various resecting member can be used to assist in the resection of an anatomy to provide for implantation of a prosthetic.

U.S. Application publication No. 2005/0137708 published on Jun. 23, 2005, entire contents of which are incorporated herein by reference, discloses a knee joint resurfacing including femoral implant and tibial implant components. The femoral implant components may be attached to the femur using screws or other fixation devices. The femoral implant component may be configured to share loads between cortical and cancellous bone material. The tibial implant components are formed in modular portions which may be assembled within the knee joint and may be free-floating or fixed to the tibial surface.

U.S. Application publication No. 2006/0064169 published on Mar. 23, 2006, entire contents of which are incorporated herein by reference, discloses numerous joint replacement implant embodiments including a total knee replacement implant including a femoral component having a wheel; and a tibial component including a shock-adsorbing component with a piston assembly and spring. The implants contain a cushioning or shock-absorbing member to dampen axial loads and other forces. In many embodiments, fluid is forced rapidly from the device wherein compression and dampening is achieved by valves or other pathways that allow for a slower return of the fluid back into the implant as the pressure is relieved.

U.S. Application publication No. 2006/0155380 published on Jul. 13, 2006, entire contents of which are incorporated herein by reference, discloses a femoral component for a total knee joint replacement having a modular structure including a number of segments, each of the segments having a femoral fixation surface for attachment to the distal end of a femur and at least one assembly surface for joining with an adjacent segment of the modular femoral component.

U.S. Application publication No. 2006/0178497 published on Aug. 10, 2006, entire contents of which are incorporated herein by reference, discloses implantable devices that include biocompatible polyurethane materials. In particular, the disclosed polyurethane materials can maintain desired elastomeric characteristics while exhibiting thermoset-like behavior and can exhibit improved characteristics so as to be suitable in load-bearing applications such as in artificial joints, including total joint replacement applications.

Oka and his associates reported that polyvinyl alcohol hydrogel (PVA-H), 'a rubber-like gel', shows its usefulness as an artificial articular cartilage (Proc Inst Mech Eng 2000; 214:59-68). As compared to polyethylene (PE), the PVA-H had a thicker fluid film under higher pressures than polyethylene (PE) did, and PVA-H had a better damping effect and better wear factor. The artificial articular cartilage made from PVA-H could be attached to the underlying bone using a composite osteochondral device made from titanium fibre mesh. The composite osteochondral device became rapidly attached to host bone by ingrowth into the supporting mesh.

Hyaluronic acid and hyaluronates (HA's), such as Synvisc, Hyalgan, Supartz, Orthovisc, Neovisc, Euflexxa/Nuflexxz, Durolane, Fermathron, Suplaysn, are available for injection into joint spaces to provide additional lubrication and treat pain associated with osteoarthritis. HA's in solution are very viscous and therefore the amount of HA per injection (about 2.0 ml) is limited by viscosity. Although injections appear to be effective, these products require multiple injections (usually 3-5) and the effectiveness lasts only for 3-6 months. The present technology is to increase molecular weight of the HA or to crosslink the HA to retard its degradation and clearance from the joint space.

Hence, repairing or replacing a torn meniscus with a meniscus wafer is suggested as a means to relieve the joint pain and to treat the knee joint accordingly. The current invention also discloses devices, methods, formulations, and instruments for treating a joint of a body.

SUMMARY OF THE INVENTION

The primary goal for treatment of osteoarthritis using hyaluronate compositions are to increase the duration of effectiveness in lubrication and pain reduction, and to reduce the number of injections required.

The secondary goal for treatment of osteoarthritis using hyaluronate compositions are to improve the effectiveness (i.e. reduce the coefficient of friction) in lubrication and pain reduction, and to provide a therapy which can have applicability in joints with relatively healthy (and therefore stiffer) cartilage as well as older and degenerated (and therefore softer) cartilage.

These objectives can be attained by increasing the residence time (half life) of the injected HA in the joint space; improving/supplementing the lubrication efficacy of HA in the joint space; and/or increasing the amount of HA per the injection.

In accordance with preferred embodiments of the present invention, some aspects of the invention provide a support structure around the circumference of the meniscus in a patient configured like a collar around a neck ("meniscal collar"), wherein the support structure comprises a body with an exterior surface characterized with enhanced boundary lubrication properties, the body being durable and abrasiveless that is made of biocompatible material selected from the group consisting of PVA hydrogel, elastomers, polypropylene, polyethylene, PEEK, and metals.

Some aspects of the invention provide meniscal augmentation using meniscal bulking agent to increase the volume of the meniscus either by injection or other filling means. The bulking agent may include biodegradable or non-biodegradable hydrogels, crosslinkable hydrogels having a higher molecular weight than those of pre-crosslinked hydrogels, and the solidifiable hydrogels having a higher viscosity index than those of pre-administered hydrogels. The bulking agent may also include the scaffold, scaffold material or scaffoldable biomaterial with cell seeding, ingrowth and regeneration capabilities. In one aspect, the mesenchymal stem cells or regenerative cells are included in the product formulation of the bulking agent. Further, some aspects of the invention provide cartilage augmentation as a process of increasing the volume of the cartilage by injection, substitution or grafting. The above cited method could be applied using imaging guidance or arthroscopically under direct viewing.

Some aspects of the invention provide a meniscal wafer, a generally planar construct, to fit between the tibial plateau/meniscus and the femoral condyle. In one embodiment, a meniscal wafer is an implant adapted to encourage tissue healing and/or mitigate pain. In one embodiment, the meniscal wafer comprises a surface antistick agent or characterized with boundary lubrication configured to reduce physical adhesion. In another embodiment, the meniscal wafer comprises an impregnated/entrapped chemical marker that is leachable or exposable as a warning after a predefined thickness of the wafer is worn out.

Some aspects of the invention provide a composite meniscus comprising a multiple component or layer structure that serves as a replacement meniscus. Components may be selected from the group consisting of metals (stainless steel, NiTi, titanium, porous titanium, and the like), lubricious polymers (PE, crosslinked PE, PP, and the like), shape memory material (polymer and metal), biodegradable polymers (PLA, PVA, PGA, PU and the like), hydrogels or hydrophilic (PVA hydrogel, polyacrylamide, and the like), and reinforcing support (porous substrate, woven fibers, filaments, and the like). Layer configurations may be selected from the group consisting of sliding layer, transition layer, ingrowth layer, backing layer, and combinations thereof. The materials and constructions disclosed herein also apply to the wafer. As disclosed herein, a meniscal wafer differs from a replacement meniscus by (1) generally being thinner and (2) attaching to or abutting the meniscus vs. the tibia or tibial cartilage.

Some aspects of the invention provide a condyle cap sized and configured to cover the femoral condoyle, the condyle cap fitting like a cap (e.g. a form fitting knit hat) over the condylar cartilage or bone. Further, some aspects of the invention provide an articular bumper sized and configured as a cap covering the tibial plateau that either may cover the meniscus or includes a replacement meniscus.

Some aspects of the invention provide a method for treating a joint by assembling the implant in-situ, wherein the implant comprises two or more components. Further, some aspects of the invention provide formed-in-place implants. In one embodiment, the method to achieve a functional low friction joint is to form one or more components out of a malleable or incompletely cured (e.g., polymerized) material in vivo or in vitro. The material is then placed in the joint space (e.g., the location of the meniscus) and then the joint cycled under load (full or partial) so the material forms into a shape appropriate to the motion.

Some aspects of the invention provide a method for manufacturing a customized anatomic implant by applying data from modern imaging modalities such as CAT and MRI to create custom implants (or tooling to manufacturing implants) with surfaces that match the anatomy and the retained natural surface.

Some aspects of the invention provide a synovial lubricant comprising phospholipids selected from the group consisting of phosphoglycerides, phosphatidyl choline, phosphatidyl ethanolamine, phosphatidyl inositol, phosphatidyl serine, diphosphatidyl glycerol, and the like.

Some aspects of the invention provide a material or a surface of the device that preferentially attracts and/or adsorbs SAPL, the surface comprising a lipid or fatty surface. In one embodiment of placing a functional phospholipid coating on a device, one may prepare the surface (e.g. plasma etch or chemically treat the surface of the device), and then expose the surface to a reactable phospholipid, such as a phosphorylcholine which contains an additional acrylic double bond, or a reactable acrylate polymer with phospholipid side chains. The phospholipid is chemically, covalently bonded to the surface of the device and to itself.

One aspect of the invention provides a material for prosthetic articular surface that has high affinity to adsorb SAPL or SAPL-like surfactant. Another aspect of this invention provides for this affinity to absorb SAPL to be incorporated into the bearing/lubricating surface of any of the devices described herein.

Some aspects of the invention provide a particulate-containing synovial lubricant that is specifically designed to overcome some of the limitations of fluids such as HA, wherein the preferred size range is about 50-150 microns with 50-100 microns considered normal desired size. The particles could be made of any biodegradable polymer, such as PLA or other hydrogel. The particles could be less than 60 A (shore durometer scale) hardness.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIGS. 7A-7B shows an exemplary meniscal liner and an exemplary combined meniscal-tibial liner.

FIG. 15 shows an illustration of a composite meniscus.

FIG. 20 shows magnetic unloading mechanism of a joint by configuring a femur having plural curved magnets which follow the arc of the femoral condyle.

DETAILED DESCRIPTION OF EXEMPLARY EMBODIMENTS

Figure 1:
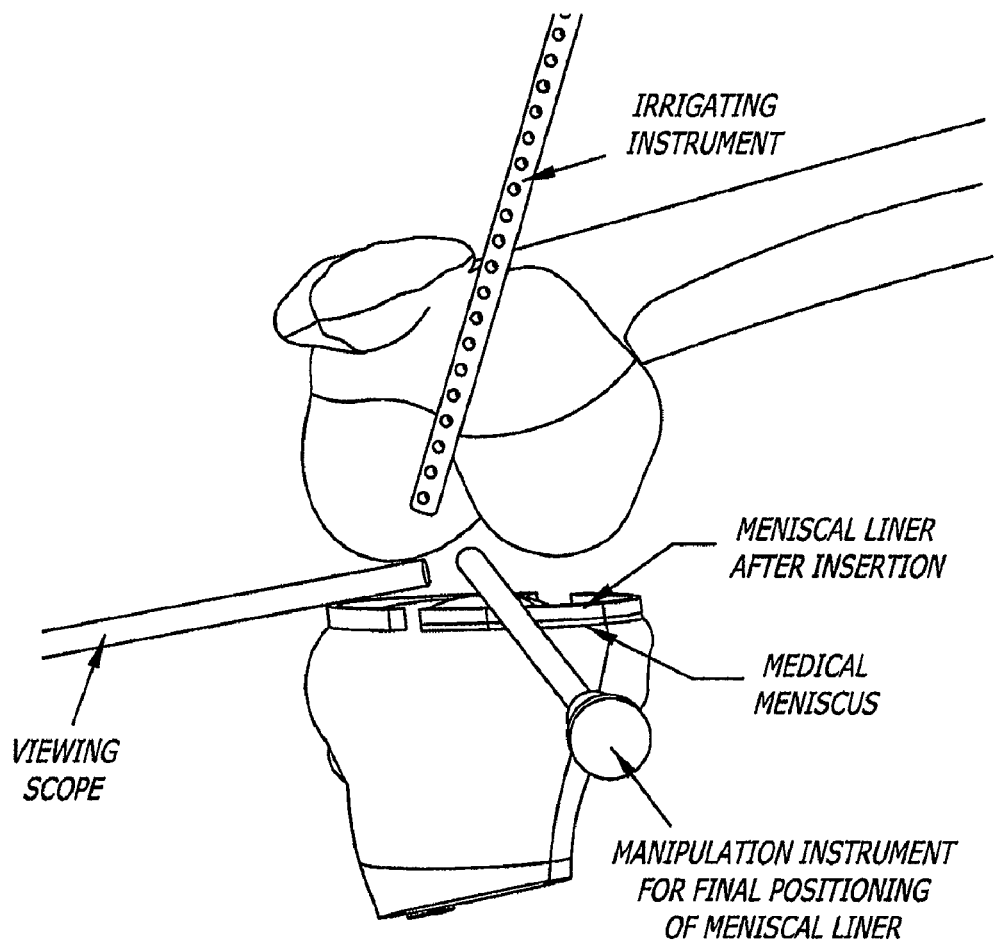
FIG. 1 shows a method of positioning of an inserted meniscal liner according to the principles of the present invention.

The preferred embodiments of the present invention described below relate particularly to medical devices for treating a joint, for example a knee join. Joints are the place where two bones meet. All of our bones, except for one (the hyoid bone in our neck), form a joint with another bone. Joints hold our bones together and allow our rigid skeleton to move. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

To better describe the invention, some terms are defined herein as follows. "Meniscal collar" in this invention is meant to refer to a support structure around the circumference of the meniscus like a collar around a neck. "Meniscal augmentation" (or "meniscal bulking agent") in this invention is meant to refer to a process of increasing the volume of the meniscus either by injection or other means. "Meniscal liner" ("meniscal wafer" or "joint interface sheet") in this invention is meant to refer to a generally planar construct that fits between the tibial plateau/meniscus and the femoral condyle. Meniscal liners are implants adapted to encourage tissue healing and/or mitigate pain. The terms meniscal liner, meniscal wafer or joint interface sheet can refer to devices that (1) cover the meniscus (only), (2) cover the tibial plateau (only) or (3) cover both. "Composite meniscus" in this invention is meant to refer to a multiple component or layer structure that serves as a replacement meniscus. "Condyle cap" in this invention is meant to refer to a prosthesis covering the femoral condoyle, fitting like a cap (hat) over the condylar cartilage or bone. "Cartilage augmentation" in this invention is meant to refer to a process of increasing the volume of the cartilage by substitution or grafting. "Articular bumper" is meant to refer to a cap covering the tibial plateau that may either cover the meniscus or include a replacement meniscus. Most of our joints are "synovial joints". They are movable joints containing a lubricating liquid called synovial fluid. Synovial joints are predominant in our limbs where mobility is important. Ligaments help provide their stability and muscles contract to produce movement.

The knee includes many components (such as the bones, the cartilage, the meniscus, and others) with many functions, including the weight bearing, flexing, and walking. Femoral and tibial condyles are the hard bones underlying the gliding surfaces of the joint. Cartilage (articular hyaline) covers the bearing surfaces of the bone and forms the primary bearing surfaces in a healthy joint. Meniscus is a secondary bearing surface between the femoral and tibial cartilages, is a cushioning layer and is a contoured surface to help guide the joint as it flexes. The bone joint includes medial and lateral compartments that essentially create two separate, though not independent, bearing surfaces. Synovial fluid serves to lubricate, and in some cases, nourish the tissue and surfaces of the joint.

A ligament is a short band of tough fibrous connective tissue composed mainly of long, stringy collagen fibres. Ligaments connect bones to other bones to form a joint. Capsular ligaments are part of the articular capsule that surrounds synovial joints. They act as mechanical reinforcements. Extra-capsular ligaments join bones together and provide joint stability. Ligaments are slightly elastic; when under tension, they gradually lengthen. This is one reason why dislocated joints must be set as quickly as possible: if the ligaments lengthen too much, then the joint will be weakened, becoming prone to future dislocations. Athletes, gymnasts, dancers, and martial artists perform stretching exercises to lengthen their ligaments, making their joints suppler. Some ligaments limit the mobility of articulations, or prevent certain movements altogether.

New approaches to knee surgery include surgical procedures as well as apparatus. One current method includes total or partial replacement of the knee joint using open surgery and arthroscopic surgery (primarily the work on cartilage, including the meniscus and ligaments). Current joint replacement surgery uses standardized, in some cases modular, component inserted through an incision. Even the procedure called "mini open" uses a 4 to 6 inches incision. Current arthroscopic procedures are performed through small ports but are limited and not useful in the treatment of osteoarthritis. These current procedures can be substantially improved.

The following outline some methods which could be applied to treat osteoarthritis and possibly other conditions of the knee.

(1) Minimally invasive joint replacement with an implant that can be assembled in-situ: (a) by assembling the implant in-situ, smaller openings are used to prepare the implant and install the implant; (b) this requires specialized implants which can include components traditionally made of one piece now made of 2 or more pieces to allow passage through smaller openings; (c) assemble components (ideally self aligning when assembled), particularly when seams occur on bearing surfaces; and (d) this should have the capability of achieving an identical clinical result to current procedures with the benefit of decreased morbidity and the potential cost of a decreased implant life.

Figure 11:
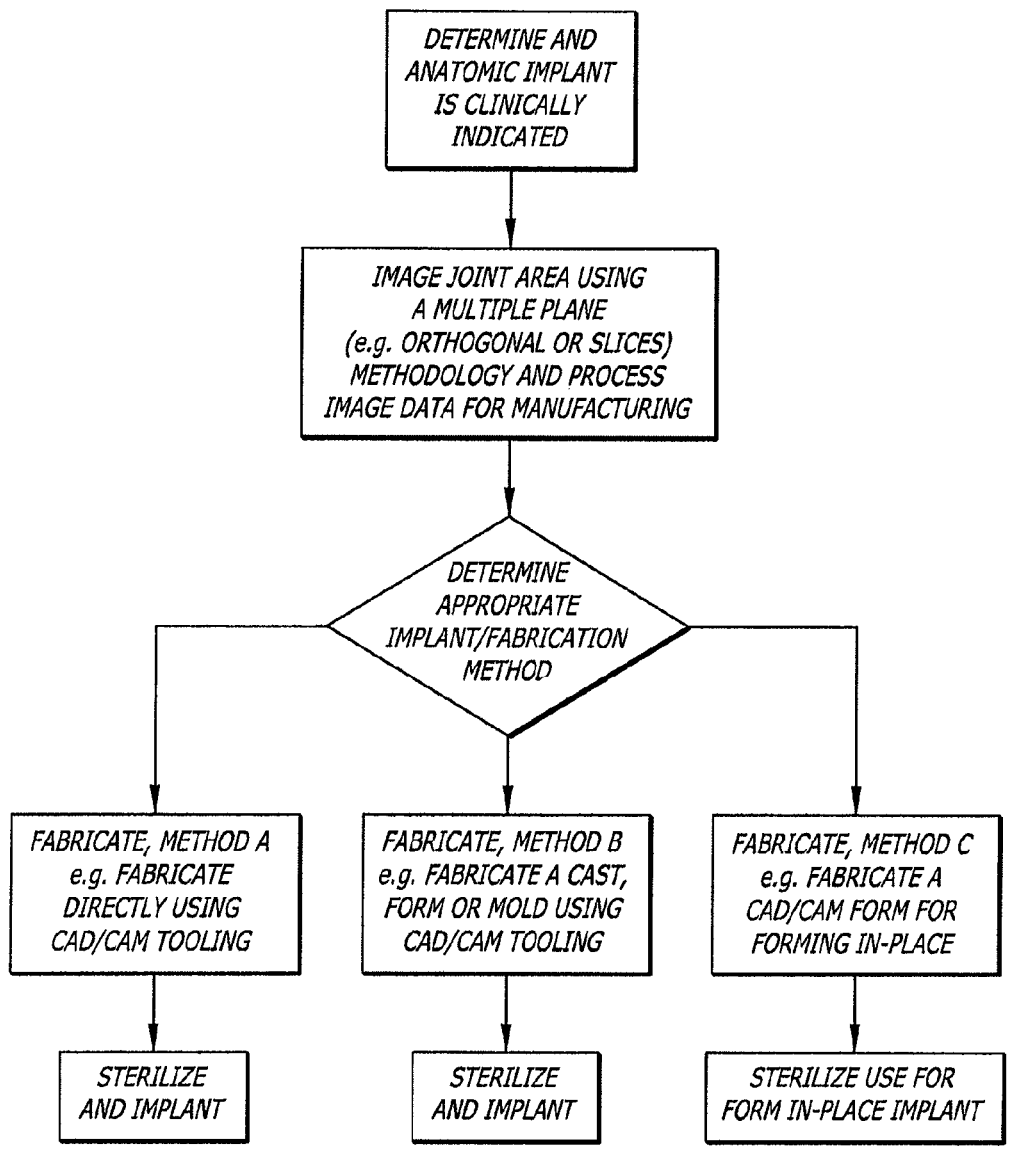
FIG. 11 shows a flowchart for manufacturing a custom anatomic implant.

(2) Customized anatomic implants: (a) current total knee replacement replaces all surfaces of the knee. Historically, and in some cases presently, replacement of selective bearing surfaces of the knee with standardized components has or is being attempted; (b) in a partial replacement where only one of a match pair of bearing surfaces is replaced and surface mismatch can lead to early failure; and (c) this method will apply data from modern imaging modalities such as CAT and MRI to create custom implants (or tooling to manufacturing implants) with surfaces that match the anatomy and the retained natural surface; (d) this method can be applied to implants which replace and/or augment existing anatomic structures; (e) these implants can be manufactured as used or in forms that can be assembled or otherwise deployed in-situ. FIG. 11 shows a flowchart for manufacturing a custom anatomic implant. This method can optionally be enhanced by use of a replaceable or regeneratable bearing surface.

(3) Formed in place implants. Another method to achieve a functional low friction joint is to form one or more components out of a malleable or incompletely cured (e.g., polymerized) material. The material is then placed in the joint space (e.g., the location of the meniscus) and then the joint cycled under load (full or partial) so the material forms into a shape appropriate to the motion. As an alternative to motion under load, a temporary mold of form can be inserted in the joint or the joint motion can be defined by an external brace or other mechanism to achieve shaping. Alternately, the material can be placed in the joint space within completely of partially preshaped forms.

(4) Internal augmentation. This method augments/supports/supplements existing structures with internal support while maintaining and/or supplementing existing bearing surfaces. Bulky cartilage or filling a bone defect could be examples of this method. This method could be applied using imaging guidance or arthroscopically under direct viewing.

(5) External augmentation. Augmentation differs from other implant schemes in that it uses rather than replaces existing structures, particularly bearing surfaces. External augmentation could include surface treatment (e.g., smoothing, coating, capping or some other means of enhancing a surface while essentially maintaining its existing structure and/or shape). This could also include minor additions/corrections/adjustments of the surfaces.

(6) Implant preparation. One significant aspect of knee joint procedures is the criticality of the alignment of the bearing surfaces as well as the quality of their attachment to underlying structures. This can be of particular interest with customized implants manufactured from imaging. Similarly externally manufactured surface implants must align with the existing structures they are designed to overlay. Systems to either artificially create or naturally identify landmarks during both imaging/design and implantation are necessary, methods and/or structures for aligning the bones and other anatomic structures may also be appropriate, Osteotomy is an accepted treatment for knee problems. In this case, a cut is made in a bone (usually the tibia) to allow the angle of the knee joint (e.g., the tibial plateau) to be adjusted with appropriate joint alignment. The principle can be applied to other approaches, for example, the meniscal liner described herein can have varying thickness (e.g., thicker on the medial side) to readjust the angle of the joint and its bearing surfaces (see FIG. 9). This could also be applied to a knee prosthesis such as a uni-knee where the side of the knee which was not replaced may show wear, thereby providing an opportunity for improved function by (1) reducing the height of the uni-knee or (2) increasing the height of the opposite side by the insertion of a spacer (for example a meniscus liner). In both these cases, aligning the joint to distribute load over both the lateral and medial side of the joint will improve joint function/longevity and/or reducing pain.

Figure 9A:
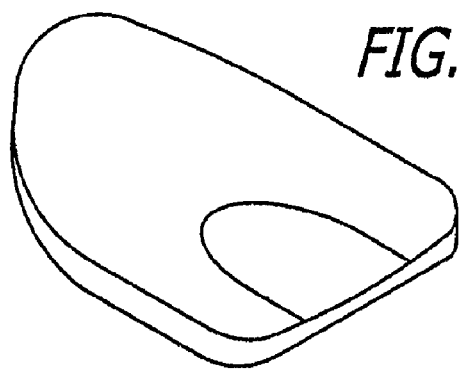
FIGS. 9A-9C shows meniscus liner variations.
Figure 9B:
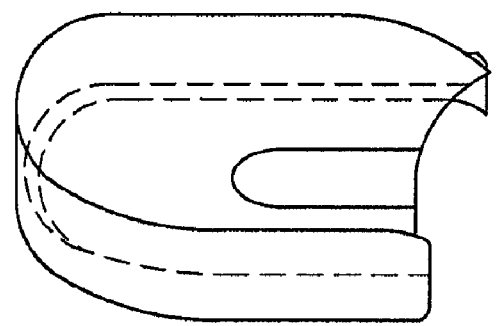
Figure 9C:
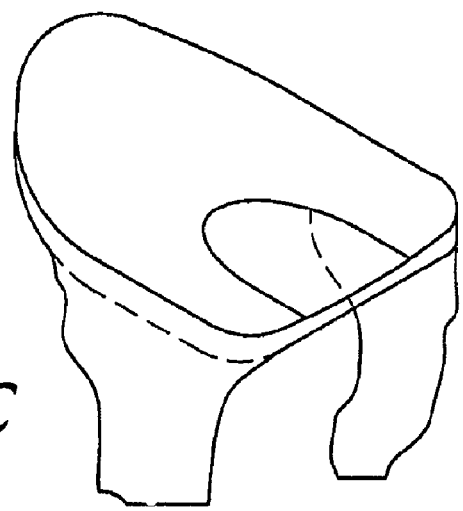

FIGS. 9A-9C shows meniscal wafer variations. One aspect of the invention (FIG. 9A) relates to a meniscal wafer with optional tibial plateau cover. This example of the meniscal wafer is shown including a tibial plateau cover. It is shown as having no special attachment means and is intended for a free-floating application. However, it could be sutured or adhesively bonded in place. Exemplary prototypes of this configuration have been assembled using 2 mm thick hydrogel adhesively bonded to a 0.5 mm thick relatively rigid polymer backing layer. In this case, the polymer backing layer was formed using vacuum forming techniques as known in the art.

A second aspect of the invention (FIG. 9B) relates to a meniscal wafer with optional meniscal retaining wing. This example of the meniscal wafer is shown including tibial plateau cover and a retention wing to extend the backing layer so it curves over and around the outer circumference of the meniscus. Though this example shows the retention wing around the entire circumference of the meniscus, partial retention wings may be also clinically indicated in certain situations. Exemplary prototypes of this configuration have been assembled from vacuum formed polymers of varying thicknesses and durometers as well as structures as described.

A third aspect of the invention (FIG. 9C) relates to a meniscal wafer with optional tibial attachment wing. This example of the meniscal wafer is shown including tibial plateau cover and a retention wing to extend the backing layer so it curves over the meniscus and extends down where it can be attached directly to the tibia (for reference, U.S. Pat. No. 4,502,161 "Prosthetic meniscus for the repair of joints" issued to Wall on Mar. 5, 1985). Exemplary prototypes of this configuration have been assembled as described.

One issue relating to meniscus treatment is the understanding of the process of meniscal degradation and sensitivity of imaging methodologies for detection of meniscal degradation.

In general the peripheral border of each meniscus is thick, convex, and attached to the inside capsule of the joint. The opposite border tapers to a thin free edge. The proximal surfaces of the menisci are concave and in contact with the condyles of the femur. The distal surfaces are flat and rest on the head of the tibia.

The medial meniscus (MM) is somewhat semicircular in form and is approximately 3.5 cm in length in the anteroposterior direction and considerably wider posteriorly than it is anteriorly. The anterior horn of the medial meniscus is attached to the tibial plateau in the area of the anterior intercondylar fossa in front of the anterior cruciate ligaments. The posterior fibers of the anterior horn attachment merge with the transverse ligament, which connects the anterior horns of the medial and lateral meniscus. The posterior horn of the medial meniscus is firmly attached to the posterior intercondylar fossa of the tibia between the attachments of the lateral meniscus. The periphery of the medial meniscus is attached to the joint capsule throughout its length. At its mid-point, the MM is more firmly attached to the femur and tibia though a condensation in the joint capsule known as the deep medial collateral ligament (MCL).

On the other hand, the lateral meniscus (LM) is almost circular and covers a larger portion of the tibial articular surface than the MM. It is approximately the same width from front to back. The anterior horn of the LM is attached to the tibia in front of the intercondylar eminence and behind the attachment of the ACL, with which it partially blends. The posterior horn of the LM is attached behind the intercondylar eminence of the tibia in front of the posterior end of the MM. There is no attachment of the LM to the lateral collateral ligament (LCL) but there is a loose peripheral attachment. The posterior horn of the LM is also attached to the femur by means of the meniscofemoral ligament.

The meniscofemoral ligament is an accessory ligament of the knee. During knee flexion, the meniscofemoral ligament pulls the posterior horn of the LM anteriorly, increasing the congruity between the meniscotibial socket and the lateral femoral condyle.

It has been demonstrated that for meniscus lesions to heal, the lesion must communicate with the peripheral blood supply. After injury within the peripheral vascular zone, a clot forms rich in inflammatory cells. This is a fibrin scaffold that eventually gets filled with cellular fibrovascular scar tissue that glues wound edges together. It becomes continuous with normal meniscus.

The extracellular matrix of menisci is composed primarily of the fibrous elements, collagen and elastin, the proteoglycans, the non-collagenous matrix proteins, and water with dissolved solutes. The water content of menisci is about 74%. The dry meniscus is composed of about 75% collagen, 8%-13% non-collagenous proteins and 1% hexosamine. Collagen fibers dominate both the morphology and composition of the meniscus. Fibers are critical for the relationship of structure and function of the tissue. The tissue called fibrocartilage because of the dominance of collagen fibers. This is apparent both at gross inspection and microscopic inspection of the tissue. The non-fibrous proteoglycans are also important for structure and function but also to the metabolism of the menisci.

The combination of low compressive stiffness and low permeability suggests that the menisci, as structures, should function as highly efficient shock absorbers. Since the combined mass of the menisci is much greater than that of the articular cartilage bearing load across the femoromeniscotibial articulation it is likely that most of the mechanical shocks generated in the knee joint by the loading is absorbed by the menisci. The deformation nature of the menisci with this low compressive (and shear) stiffness and permeability show them to distribute load well in the knee.

The strong ligaments, (cruciates and collaterals) menisci and capsule, and the musculature constitute the primary stabilizers of the knee. These structures and muscles around the knee constitute a complete biomechanical system in which the tibia can move with respect to the femur in many planes, yet also support the high loads (more than 5 times body weight) commonly found in the joint during daily activities.

Figure 12:
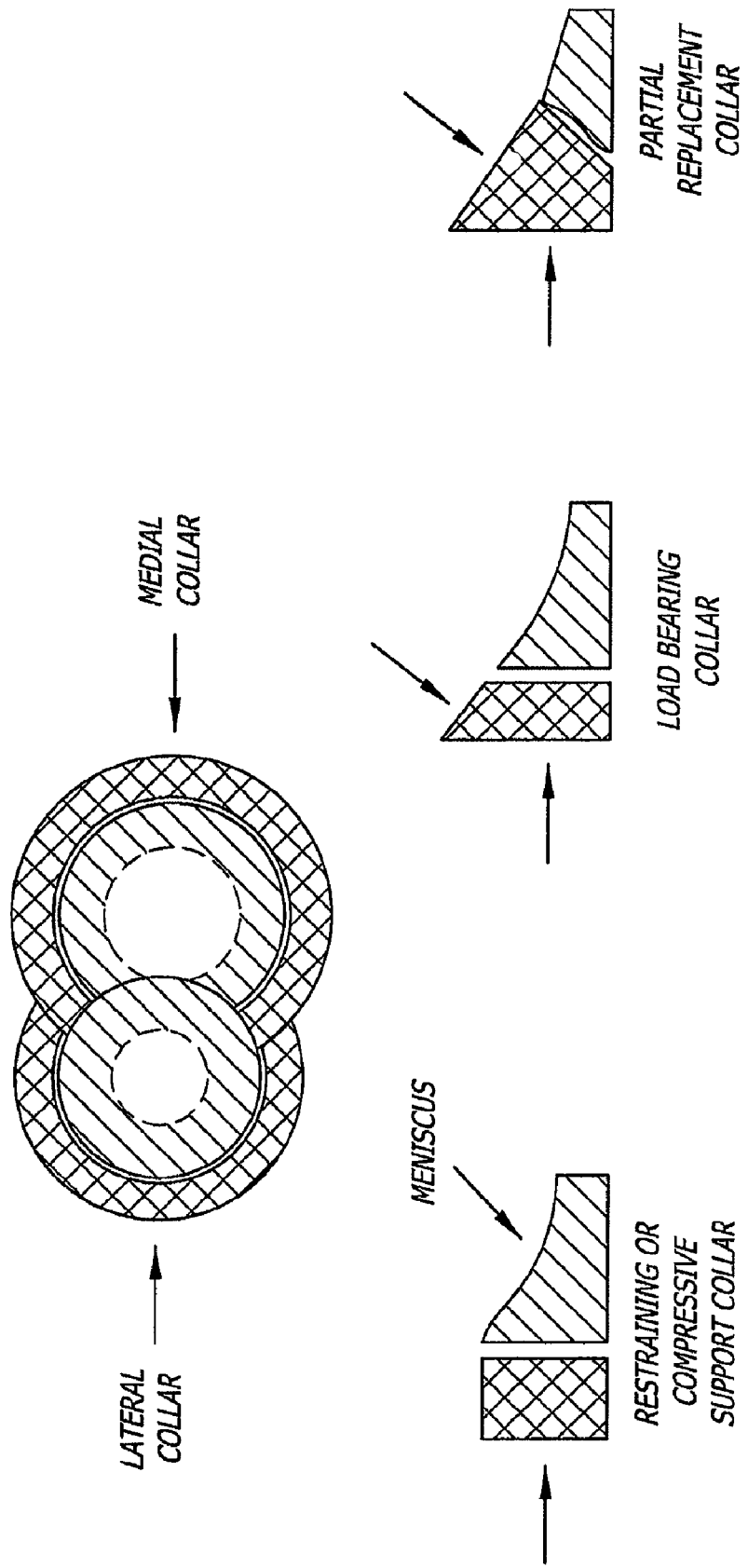
FIG. 12 shows load transmission in a meniscal collar.

Congruency is important in load transmission through the femoromeniscotibial articulation. It has been reported that the meniscus bears 50-80% of the compressive load of the knee joint. It was reported that removal of 15-34% of the meniscus increases contact pressure by more than 350%. The meniscal collar is a minimally invasive implant device intended to augment the function of the meniscus. The basic idea is a "collar" or rim placed around one or both of the menisci. One embodiment is shown in FIG. 12 for illustration.

The meniscal collar (MC) can be placed in an open procedure, arthroscopically using a percutaneous procedure, or a combination thereof. In a percutaneous approach, a guidewire would be passed around the meniscus and then the MC could be pulled into position by the wire or, with an appropriate lumen incorporated into the MC, pushed over the wire into position. FIG. 1 shows positioning of an inserted meniscal liner. Though the technique shown in FIG. 1 is for positioning a meniscal liner, the similar technique can also be used in positioning a meniscal collar.

The MC can be constructed from metal such as stainless steel or tantalum, a lubricious polymer such as polyethylene (PE) or crosslinked polyethylene or from a lubricating hydrogel such as polyvinyl alcohol. The MC could optionally have reinforcing mesh or wire or load transmitting wire or a removable wire that could be placed in a lumen such as a guidewire lumen. The MC could also be constructed, wholly, in combination or in part, from a shape memory and/or biodegradable polymer such as those described in U.S. Pat. No. 6,720,402 and U.S. Pat. No. 6,160,084, entire contents of both are incorporated herein by reference.

The MC could have a variety of cross-section shapes including round, oblong or custom shapes to mimic the load bearing surfaces of the meniscus. The MC could be a single continuous shape or change over the perimeter of the meniscus. The MC could be smooth, contoured, or notched. Notched construction can facilitate flexing of the MC if constructed by a more rigid polymer.

An MC could be constructed in many configurations, such as a lateral medial construct, a combined heart construct, or a combined pretzel construct.

Various shapes can accomplish certain goals such as avoiding the cruciate ligaments or transmit greater forces (the "pretzel" shape as shown above can have legs that can be locked and/or tightened). These means to effect locking and/or tightening can be optionally reversible and could use structures such as a ratchet similar to that used in a "zip-tie", a series of balls with one or more mating sockets or other means well know in the fastener art.

The meniscal collar may function directly (by providing a load bearing surface) or indirectly (by deforming and/or containing) to supplement the meniscus so it can better support loads. Or the meniscal collar may function both in combination.

One issue related to the use of a meniscal collar is the fact that meniscal innervation and vasculature is on its periphery. MC design should optionally incorporate means such as cushioning (e.g., a hydrogel lining) or dimensioning (e.g., sizing to avoid constant pressure on the meniscus) to avoid pain and/or ischemia. Reinforcing of the MC can be, for example, NiTi, stainless steel, other rigid polymers, or shape memory material. Additionally the capsule of the knee joint surrounds the meniscus (as well as the rest of the joint). Though in most clinical situations the meniscal collar would be placed within the joint capsule, if clinically indicated, certain configurations of a meniscal collar (not the pretzel) could be placed on the exterior surface of the capsule.

The MC design and shapes could be asymmetric in the support of the knee and could work in extension, flexion or both. The MC can be "free floating" or attached to the tibial and/or the meniscus. The MC could be constructed of layered material where some layers are optimized for their lubricious load bearing (for example, PE) while other layers could be used for cushioning (e.g., a hydrogel or polyurethane). Attachment can be using fasteners or ingrowth where a portion of the device in contact with the tibial plateau can be, for example, sintered porous tantalum.

Meniscal Wafer/Liner

Figure 8:
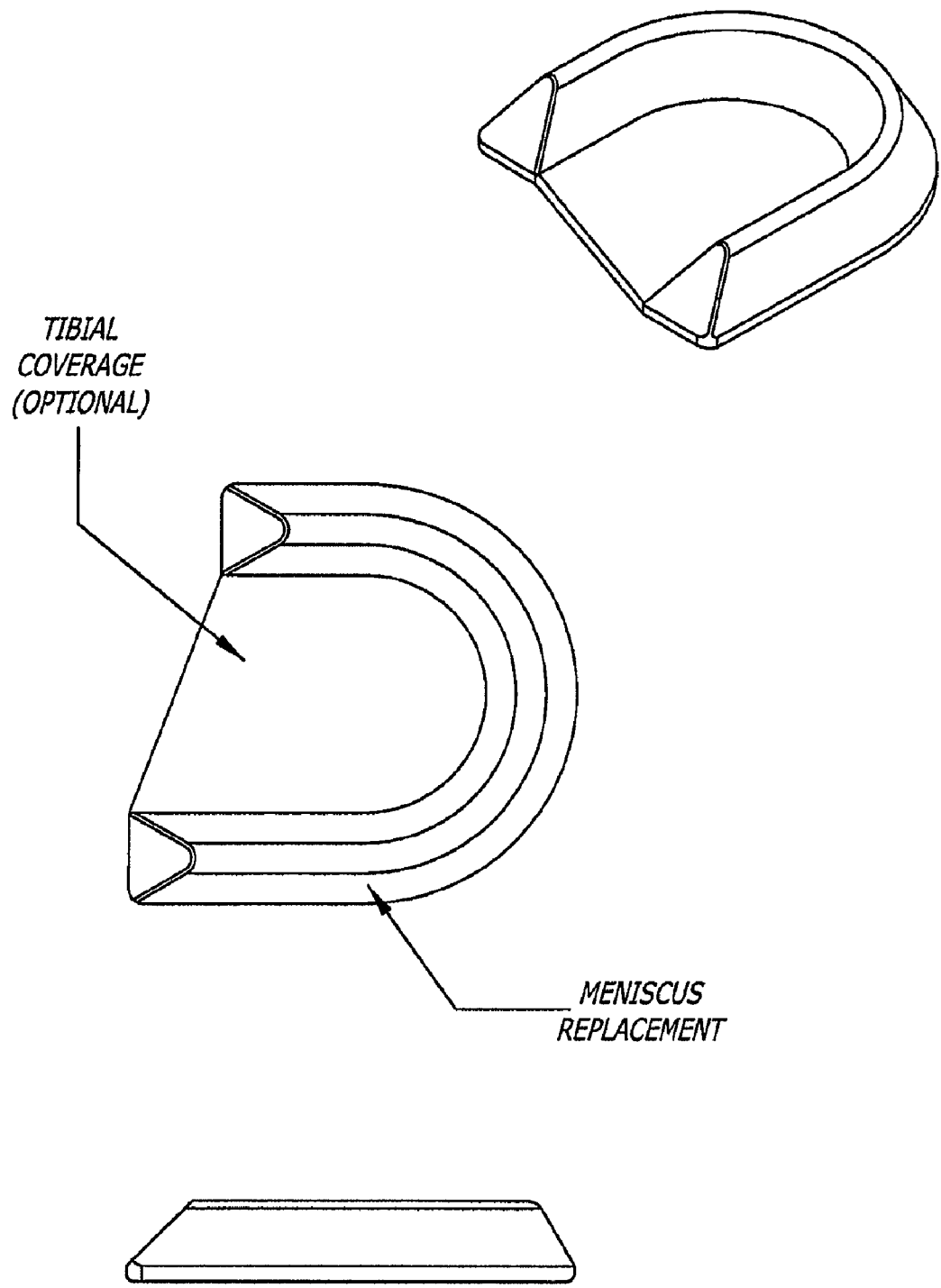
FIG. 8 shows a prototype of meniscus replacement.

Some special characteristics of one example of the proposed meniscal wafer of the present invention are shown below: (1) a PVA (polyvinyl alcohol) backing plate with appropriate hydrogels (for example, a PVA hydrogel) such that when wet, the hydrogels are very slippery and the hydro gels provide good cushioning; (2) the meniscal wafer might have an attachment wing (in some cases); (3) the meniscal wafer might have a crescent-shaped NiTi reinforcement (or reinforced by other material, configuration, or composite characteristics) around the periphery of the hydrogel; (4) the thickness of the meniscal wafer could be at least 1 mm, preferably 3 mm or more; (5) the backing plate is material that can be manufactured as an integral or chemically compatible (for bonding) to the hydrogel with desired mechanical integrity and properties. FIG. 8 shows a combined meniscal-tibial implant whereas FIGS. 7A-7B shows an exemplary meniscal liner and an exemplary combined meniscal-tibial liner of the present invention. The meniscal-tibial implant is herein meant to be the same as the replacement meniscus with combined meniscus-tibia. For illustration, FIGS. 5 and 6 show the three variations of the meniscal, tibial and combined liners.

Figure 2:
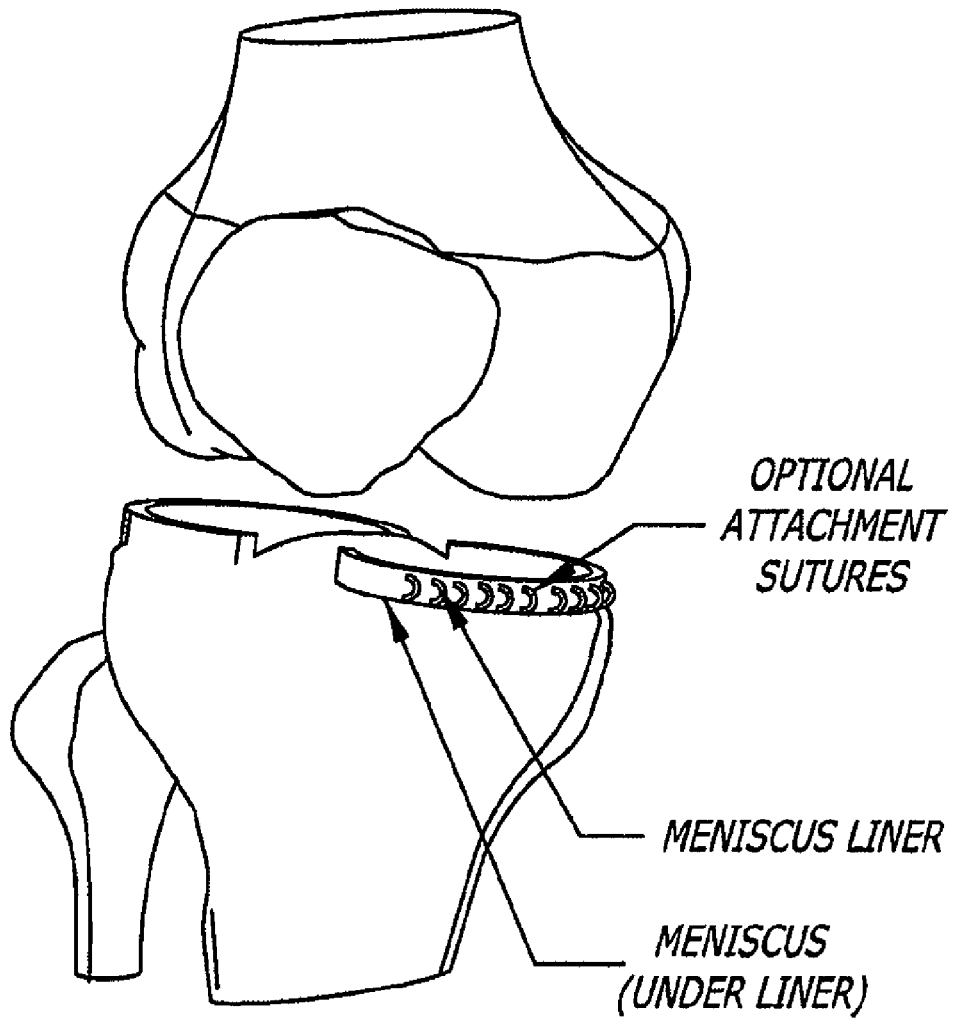
FIG. 2 shows a method of attachment of a meniscal liner using sutures.
Figure 4:
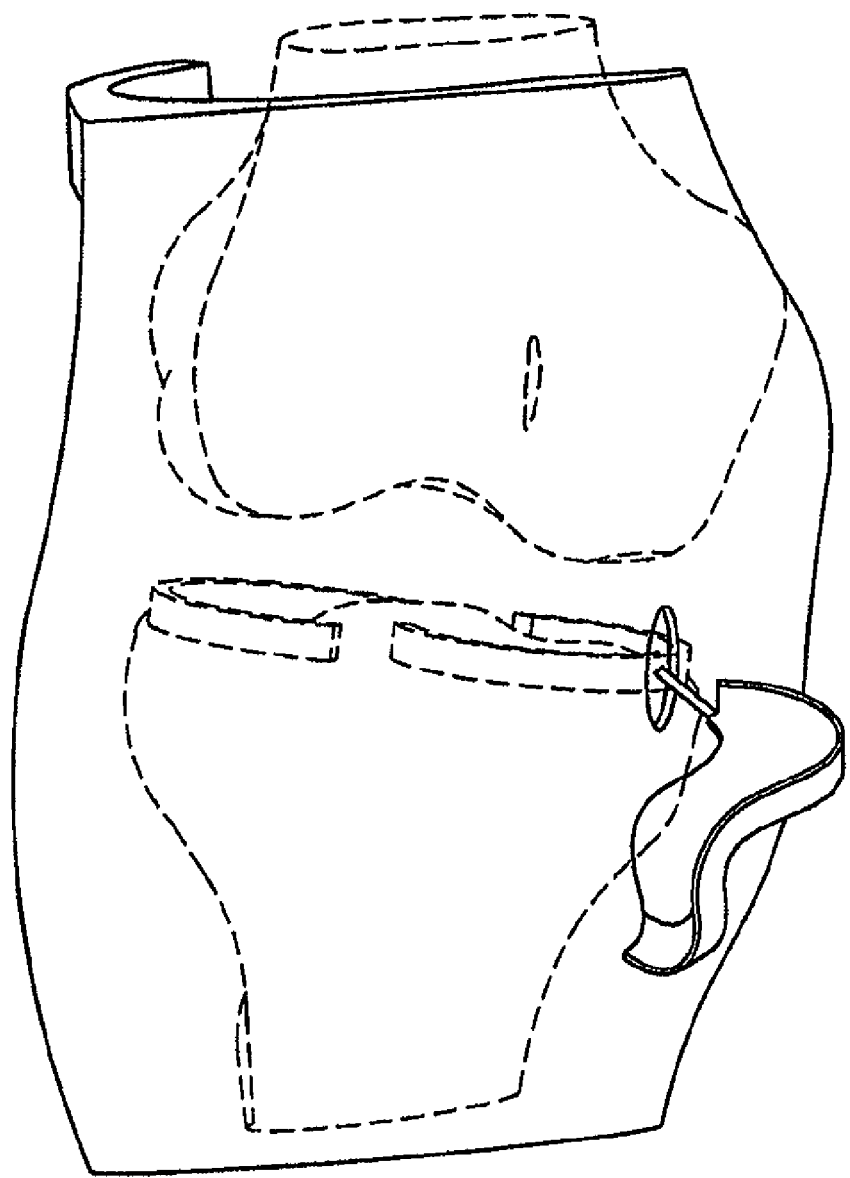
FIG. 4 shows insertion of a meniscal liner without use of an insertion cannula.
Figure 5A:
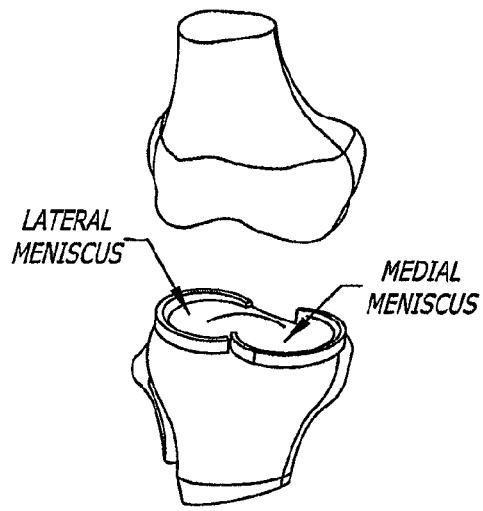
FIGS. 5A-5D show placement of a meniscal implant.
Figure 5B:
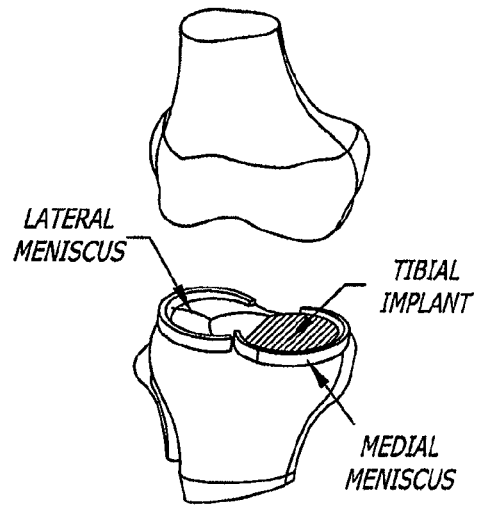
Figure 5C:
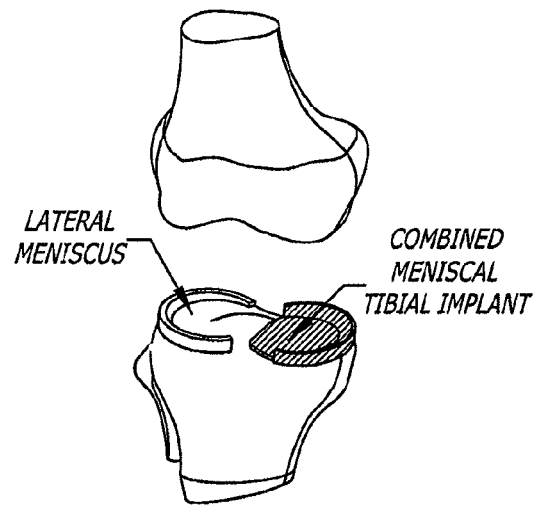
Figure 5D:
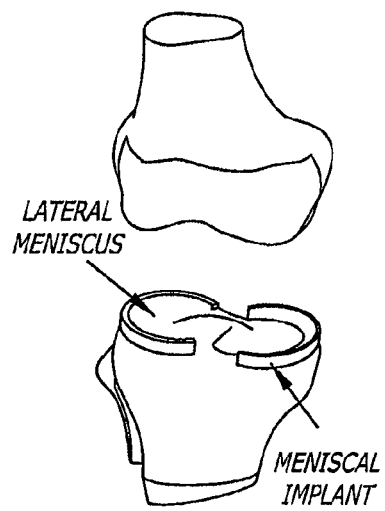
Figure 6A:
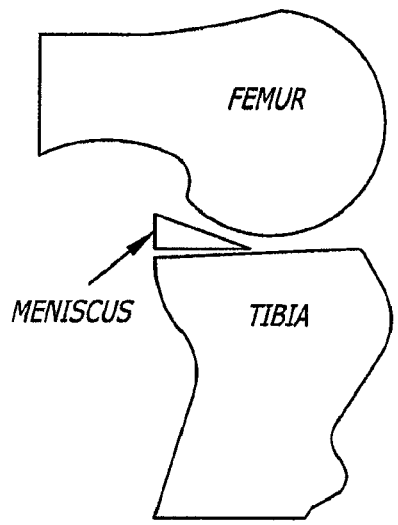
FIG. 6 shows a combined meniscal-tibial implant.
Figure 6B:
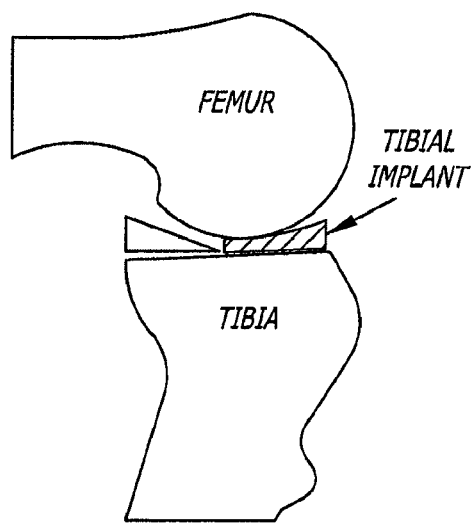
Figure 6C:
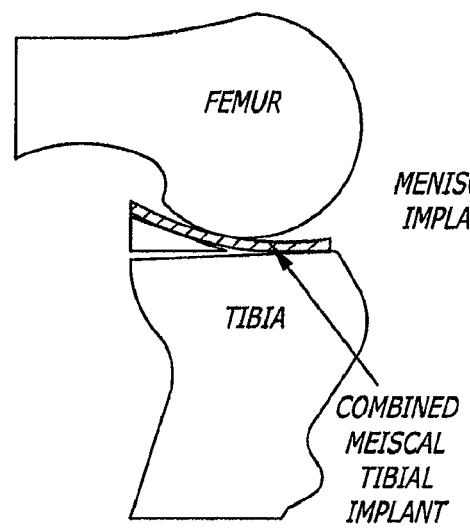
Figure 6D:
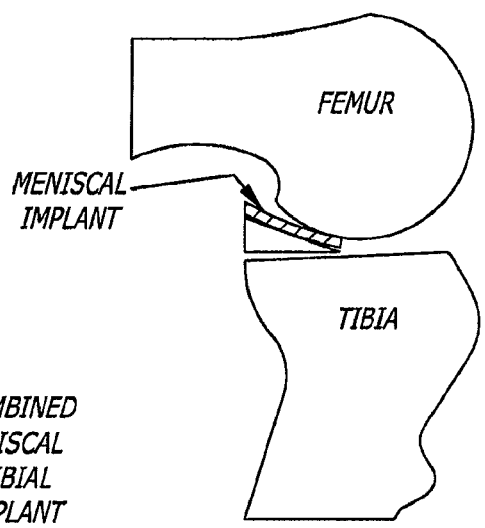

A meniscal wafer/liner of this construction can be constructed of materials with flexibility to allow implantation through a small skin incision. By ways of illustration, FIGS. 5B-5D and 6B-6D show placement of a meniscal liner, where FIGS. 5A and 6A show the corresponding anatomy with no implant. Sutures, or a wing if included in the device, can be grasped from another port or incision and used to pull the device through the skin and into position in the knee. FIG. 2 shows attachment of a meniscal liner using sutures. A meniscus liner can also be inserted with a delivery catheter (see FIG. 3) or without use of an insertion cannula (see FIG. 4).

EXAMPLE NO. 1

Meniscal Wafer Manufacturing

A meniscal wafer (MW) is a medical device implanted via an arthroscope into the knee joint space (see FIG. 1) to act as a support and bearing wear surface between the femoral condyle and the meniscus/tibial plateau. It is for (1) use in partial or total meniscectomy to supplement or provide meniscus function and articulating surface (to minimize joint degradation), (2) use in place or partial or total meniscectomy (to delay joint degradation), (3) use after arthroscopic clean-up of osteoarthritis (OA) joint to provide fresh articulating surface and improve biomechanics (to delay total knee replacement, for example), and/or (4) to adjust the alignment of the joint though height supplementation. Meniscal wafers can be used on the medial, lateral or both sides of one or both joints. Meniscal wafers can (i) cover the meniscus (only), (ii) cover the tibial plateau (only) or (iii) cover both. FIG. 5 (B-D) shows placement of a meniscal wafer.

Figure 3:
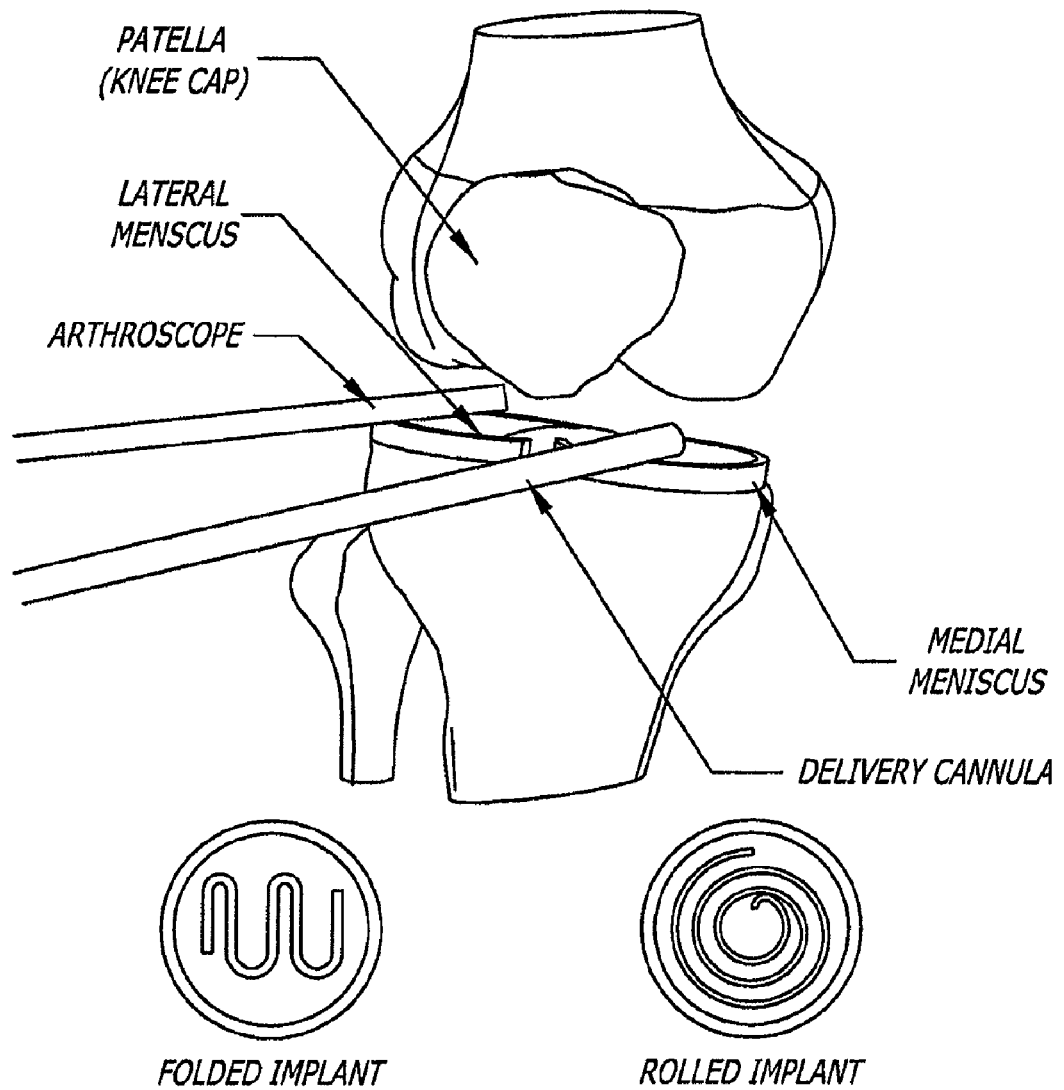
FIG. 3 shows insertion of a meniscal liner implant using a delivery cannula.

The manufactured meniscal wafer has one or some of the following characteristics:
  Insertion via an arthroscope and through a cannula (folded or rolled configuration as shown in FIG. 3) or through a skin incision (as demonstrated in FIG. 4, where arthroscope and tools are omitted for clarity);
  Permanent, non-biodegradable device with a functional lifetime of 3+ years;
  Non-fixed or floating design, limited in movement by mechanical/physical means, such as a passive stopper configuration at a periphery of the meniscal wafer;
  Medial, lateral and dual compartment designs for various indications/presentations; able to be trimmed (or malleable) by physicians;
  Materials can be polymeric (e.g. crystalline PVA, crosslinked PU, PEEK, UHMW PE) or a soft metal (e.g. Ti, non-ferrous, alloy). Reinforcing mesh (e.g. carbon fiber) may be required for tear strength or combinations of the above;
  Lubricious materials (e.g. hydrogel or surfactant) or coating on device surface by adsorption, chemical bonding (e.g. phospholipids) or ion implantation (sputtering);
  Sterilization by ETO, $H_2O_2$, or radiation (gamma or e-beam); and
  Shelf life of about 2 years or more.
  FIG. 7B shows a combined meniscal/tibial liner for reference.

The meniscal wafer or liner may need to be well attached, particularly to resist shear forces. The anatomy might make it difficult to secure at the perimeter. One approach is to have a prong or interlocking fiber filled backing, like Velcro that will stick to tissue when implanted as one approach for anchoring purposes. An ingrowth encouraging material as described above (e.g. sintered porous tantalum) may be appropriate if, in a specific clinical condition, it is desirable to fix the device to the tibial plateau. The attachment means can be over all or part of the area of the meniscal wafer (MW). Alternately, the meniscal wafer may be sutured to the meniscus (see FIG. 2).

It is possible that a sheet would fragment, probably painfully, when it fails. Fiber reinforced sheet may require replacement before it wears to the reinforcing layer which will be abrasive. A sheet constructed from metal may fail too and would probably accelerate cartilage degradation. It may be desirable for a meniscal wafer to have the property of degradation-on-demand or other means described herein to facilitate device removal. This may comprise a step of injecting a medically compatible solvent, for example DMSO, into the knee that will quickly degrade the implant (but preserve the surrounding tissue) so it can be removed by flushing.

Active electronic detection could be built in for detection of incipient failure. One example is to incorporate radiopaque and/or MRI readable layers so device thickness and/or wear can be seen at a routine doctor visit (for example, with ferromagnetic tags) or wear releases something easily (and painlessly) detectable, for example, methylene blue which turns urine blue.

In the past, porous material made of an aromatic polyurethane were successfully used for meniscal reconstruction in dogs. An aliphatic PU network, synthesized by crosslinking poly($\epsilon$-caprolactone) and 1,4-trans-cyclohexane diisocyanate with glycerol, was used (Biomaterial, September 1995). Dislocation caused by tearing out of the sutures was found to be a problem because the tear resistance of the material was relatively low. Meniscal prosthesis turned out to induce fibrocartilage upon implantation, and degeneration of articular cartilage was less severe than after meniscectomy.

Figure 13A:
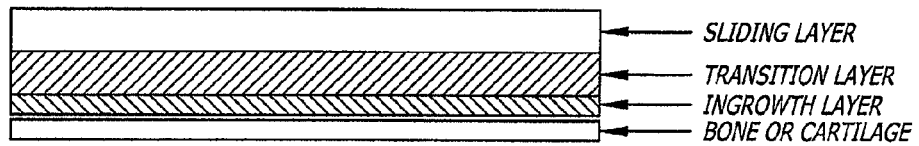
FIG. 13 shows a meniscal prosthesis with: (A) layer configuration; and (B) structure configuration.
Figure 13B:
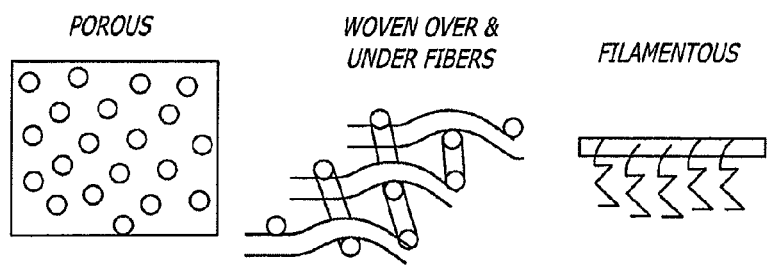

In the following embodiment, simple layers are shown with a porous, woven or filamentous layer for ingrowth (see FIG. 13B). Sintered porous materials such as tantalum are well known in the art. They are created by compressing and bonding the particles so there are a series of connected voids (or open pores) between the particles. The size of the voids are related to the size and shape of the particles as well as the processing (sintering) parameters.

By ways of illustration, an exemplary meniscal liner and an exemplary combined meniscal-tibial liner have been shown in FIG. 7A and FIG. 7B.

Lubricating Fluid

The synovium (synovial membrane) generates and contains the synovial fluid. The inner membrane of synovial joints is called the synovial membrane, which secrets synovial fluid into the joint cavity. This fluid forms a thin layer (approximately 50 micrometers) at the surface of cartilage, but also seeps into the articular cartilage filling any empty space. The fluid within articular cartilage effectively serves as a synovial fluid reserve. During normal movement, the synovial fluid held within the cartilage is squeezed out mechanically (so-called weeping lubrication) to maintain a layer of fluid on the cartilage surface. There is about 3.5 ml of synovial fluid bathes the knee joint. Some lubricant or lubricant component is adsorbed by the articular cartilage and then released under pressure.

Lubrication may be categorized as hydrodynamic lubrication, elasto-hydrodynamic lubrication, transition from hydrodynamic to elasto-hydrodynamic to boundary lubrication, and boundary lubrication. Any substance acting as a boundary lubricant must first be adsorbed or otherwise bound to the surface before it can impart solid-to-solid boundary lubrication. The stronger the binding and the more cohesive the adsorbed lining, the better is the lubrication and resistance to wear under load. Synovial fluid is believed to act as a vehicle for transporting the boundary lubricant to its site of adsorption. Hyaluronic acid is often injected into joints to provide "visco-supplementation", which would enhance hydrodynamic lubrication in nonload-bearing joints and other joints when not subjected to load. Basically, it possesses no load-bearing capability unless surface-active phospholipid (SAPL) or equivalent is incorporated.

Some aspects of the invention relate to a meniscal device comprising a support structure around circumference of a meniscus in a patient, wherein the support structure comprises a body with an exterior surface characterized with enhanced boundary lubrication, the body being made of biocompatible material selected from the group consisting of PVA hydrogel, elastomers, polypropylene, polyethylene, PEEK, and metals. In one embodiment, the device comprises a meniscal collar device, a meniscal wafer device, a meniscal liner device and the like.

In one preferred embodiment, the enhanced boundary lubrication comprises means for attracting or adsorbing a surface-active phospholipid, for coating a functional phospholipid on the device, and for coating a reactable acrylate polymer with phospholipid side chains.

One group of substances much used in the physical sciences as boundary lubricants for transforming hydrophilic subphases to hydrophobic surfaces are surfactants. Moreover, SAPL, known as a surfactant in the lung, is present in the SF of normal joints in appreciable quantities. These small molecules bind to amino acid groups that comprise the protein chains in proteoglycans such as lubricin. The lipid content of cartilage amounts to 0.3 to 4% and lipid is composed of three basic components, cholesterol, triglycerides, and phospholipids. The first two predominate in most sites in which fat is located in the body. In the normal joint and in the lung, the major component (about 60%) is phospholipid, whereas a major sub-fraction of phospholipid is phosphatidylcholine.

Phospholipids are a class of lipids formed from four components: fatty acids, a negatively-charged phosphate group, nitrogen containing alcohol and a backbone. Phospholipids with a glycerol backbone are known as glycerophospholipids or phosphoglycerides. There is only one type of phospholipid with a sphingosine backbone, sphingomyelin. Phospholipids are a major component of all biological membranes, along with glycolipids and cholesterol. In phosphoglycerides, the carboxyl group of each fatty acid is esterified to the hydroxyl groups on carbon-1 and carbon-2. The phosphate group is attached to carbon-3 by an ester link. This molecule, known as aphosphatidate, is present in small quantities in membranes, but is also a precursor for the other phosphoglycerides. One aspect of the invention relate to a synovial lubricant comprising phospholipids selected from the group consisting of phosphoglycerides, phosphatidyl choline, phosphatidyl ethanolamine, phosphatidyl inositol, phosphatidyl serine, diphosphatidyl glycerol, and the like.

Phosphatidyl choline is the major component of lecithin. It is also a source for choline in the synthesis of acetylcholine in cholinergic neurons. Phosphatidyl ethanolamine is the major component of cephalin. In phosphoglyceride synthesis, phosphatidates must be activated first. Phospholipids can be formed from an activated diacylglycerol or an activated alcohol. Phosphatidyl serine and phosphatidyl inositol are formed from a phosphoester linkage between the hydroxyl of an alcohol (serine or inositol) and cytidine diphosphodiacylglycerol (CDP-diacylglycerol).

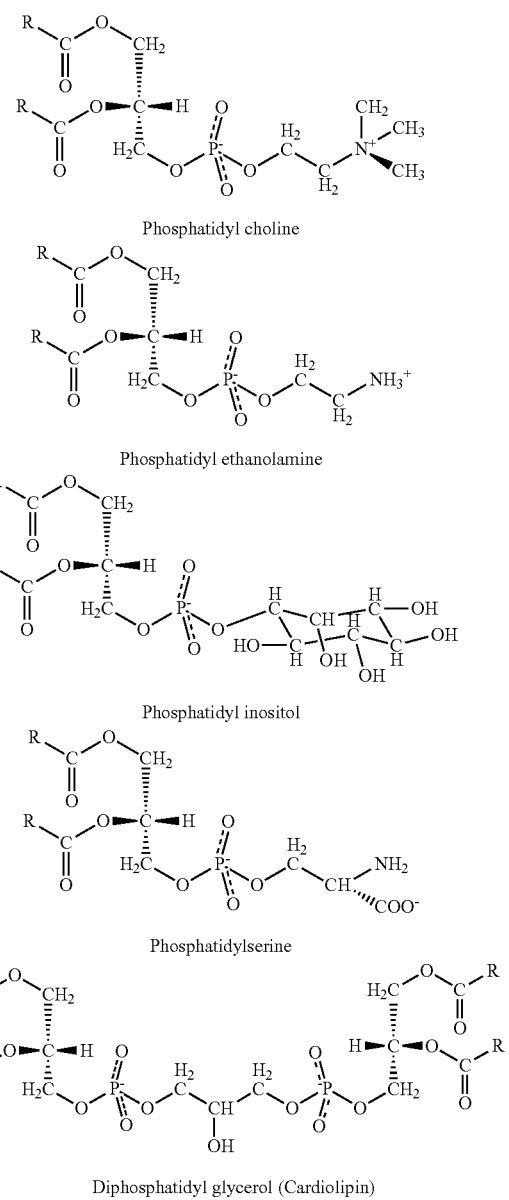

Some aspects of the invention relate to a material or a surface of the device that preferentially attracts and/or adsorbs SAPL, comprising a lipid or fatty surface. In one embodiment of placing a functional phospholipid coating on a device, one must prepare the surface (e.g. plasma etch or chemically treat the surface of the device), and then expose the surface to a reactable phospholipid, such as a phosphorylcholine which contains an additional acrylic double bond, or a reactable acrylate polymer with phospholipid side chains. The phosphatidylserine could also be used. The phospholipid must be chemically, covalently bonded to the surface of the device and to itself. Without a good covalent bonding, the coating will rub off. Hydrophilic coatings are applied in the same manner to the device surface.

Phospholipids (PL's) are naturally present in blood, plasma, serum, etc. A mixed protein layer is deposited on a device's surface within minutes to hours after body contact. PL's will adsorb on the surface of a device soon after deposition of the protein layer. Investigators have dip coated PL's from solution onto an artificial surface and then exposed the device to blood or plasma to get an even richer PL layer. However, this coating will not be sturdy enough for a wear surface.

The capability of SAPL to act as a boundary lubricant was first recognized in the thoracic cavity, in which frictionless sliding of the lungs is needed to reduce the work of breathing. SAPL also acts as a release (antistick) agent. If two normal articular surfaces are clamped together, they do not stick. However, if the SAPL lining (the outermost phospholipid zone) of the articular cartilage is removed by a lipid solvent, then they would stick. Some aspects of the invention relate to a meniscal wafer, meniscal liner or a meniscal implant that comprises a surface antistick agent or characterized with boundary lubrication configured to reduce physical adhesion. Thus, a nonstick lining of SAPL-like surfactant would prevent adhesive wear of the device of the invention.

One aspect of the invention provides a material for prosthetic articular surface that has high affinity to adsorb SAPL like surfactant. Another aspect of this invention provides for this affinity to absorb SAPL to be incorporated into the bearing/lubricating surface of any of the devices described herein.

It is speculated that changes in synovial fluid properties accelerate meniscal degradation. The purpose of lubricating the joint is to relieve pain, not to mask pain. Synovial fluid can be classified into normal, non-inflammatory, inflammatory, septic and hemorrhagic fluids. Osteoarthritis and trauma are in the non-inflammatory class. Rheumatoid arthritis is inflammatory whereas trauma can also be hemorrhagic.

To improve lubrication of the joints, it is one embodiment of the present invention to insert a minimal invasive recirculation pump. Articular cartilage is elastic, fluid-filled, and backed by a relatively impervious layer of calcified cartilage and bone. This means that load-induced compression of cartilage would force interstitial fluid to flow laterally within the tissue and to surface through adjacent cartilage. As that area, in turn, becomes load bearing, it is partially protected by the newly expressed fluid above it. This is a special form of hydrodynamic lubrication, so-called because the dynamic motion of the bearing areas produces an aqueous layer that separates and protects the contact points.

Boundary layer lubrication is the second major low-friction characteristic of normal joints. Some investigators have speculated that the critical factor is a small glycoprotein called lubricin. The lubricating properties of this synovium-derived molecule are highly specific and depend on its ability to bind to articular cartilage where it retains a protective layer of water molecules. Lubricin is not effective in artificial systems and thus does not lubricate artificial joints.

Joints such as the knee are bathed in lubricating synovial fluid. If additional synovial fluid could be directed into the space within the meniscus between the condyle and tibial plateau, improved lubrication could be achieved. Similarly, if the synovial fluid can be maintained in and around the surface of the meniscus and/or between the cartilage of the femoral condyle and tibial plateau during gait, improved lubrication could be achieved. Similarly, if the synovial fluid in the meniscus (between the condyle and the tibial plateau) could be pressurized, force would be applied to separate and reduce the friction between the condyle and tibial plateau (as with pressurized "air" bearings). And thereby, the same effect as improved lubrication can be achieved.

Valves have been proposed for use with synovial fluid. U.S. Pat. No. 5,870,303 proposes a valve to relieve excess pressure in synovial fluid. U.S. Application publication No. 2006/0064169 proposes a valved cushion where valves control the entrance and/or exit of fluid into/out of a reservoir and thereby control a cushioning effect during gait. Some aspects of the invention relate to a system including valves and a reservoir as described in U.S. Application publication No. 2006/0064169 with fluid being forced from the reservoir into the meniscal space between the condyle and tibial plateau for the purposes of improved lubrication.

The pumping of synovial fluid for the purposes of lubrication could be optionally improved by: (1) providing any piston type means to increase the pressure of the pumped fluid over the pressure between the meniscus, condyle and tibial plateau by sizing the piston with an area smaller than the tibial plateau and meniscus so the weight of walking acts over a smaller area and generating a higher pressure and (2) using a meniscal collar or other means to entrap the pressurized fluid within the tibial plateau and meniscus. An advantage of the use of such piston means is that controlling the piston areas in a two chamber pump can allow pressure multiplication to provide high pressure synovial fluid within the joint. These pumps could be externally powered, indirectly powered by gait (for example a piezoelectric crystal could generate energy to power a pump) or directly powered by gait such as the above referenced U.S. Application publication No. 2006/0064169. Alternately, other pumping and/or entrapment means such as described below can be used to accomplish improved lubrication.

Though higher pressure pumping can be advantageous, pumping additional synovial fluid into the joint space when unloaded or open during the gait cycle can also result in improved lubrication. One such lower pressure embodiment illustrates a non-piston meniscal pump being placed in meniscus to pump synovial fluid into meniscus.

An extension of the meniscal pump disclosed above could be an entire replacement meniscus designed to be a pump.

The synovial fluid saturated compressive pumping layer stores fluid until compression forces the fluid out on to the tibial plateau. Relief of compressing refills the layer. In one embodiment, a device surface may contain sponge interstices to transiently store synovial fluid or made lipophilic to attract SAPL by treating the surface with reactable chemicals containing lipid components or by dip-coating lipids onto the surface. The cartilage-like mechanical properties of the device will reside with the core material.

The outflow valve is shown as a thinned portion of the bearing surface which allows it to move upward and thereby open under internal pressure when weight is applied. The thinned area also has room to move because it does not come in contact with the condyle. The inflow valve deflects inward and would seal under internal pressure. The inflow flap would incorporate means to restrict its outward movement and create a seal when internal pressure is created by compression of the meniscus.

The lubrication of the knee joints provided by synovial fluid is necessary for joint function and longevity. It has been reported that the lubricating ability of synovial fluid can change due to or in response to, e.g., acute injury or arthritis. Hyaluronic acid (HA) is used clinically to improve the lubricating ability of synovial fluid. However, its effectiveness and length of action (time wise) has been questioned or is not as long as desired. Burdick et al. in U.S. Application publication No. 2005/0164981 and U.S. Pat. No. 6,800,298 proposed a combination of a dextran hydrogel and a phospholipid.

Some aspects of the invention relate to a particulate synovial lubricant that is specifically designed to overcome some of the limitations of fluids such as HA which have very limited half lives when injected into joints. The invention is unique in that (1) it recognizes that one aspect of creating an artificial lubricant, can be the criticality of particle size for function and longevity; (2) it provides for material specifically different fluid than dextran and phospholipid; and (3) it defines preferred material parameters. For size consideration, particles should be greater than 10 microns to avoid macrophage phagocytosis and greater than 30-40 microns to avoid particles escaping into the capillaries or other vasculature. As mentioned herein, the typical SAPL lubricating layer is approximately 50 microns.

It is suggested that large particle sizes (100 microns) may keep an artificial lubricant out of the bursae. The bursae are synovial fluid filled sacs which form a lubricating interface between soft tissue and bone; e.g. between the patellar tendon and the underlying bone. Bursae occur at sites of shearing in subcutaneous tissue or between deeper tissues such as muscle groups and fascia. Many bursae develop during growth but new or adventitious bursae can occur at sites of occupational friction. The preferred size range is 50-150 microns with 50-100 microns considered normal desired size.

For materials consideration, though longevity of treatment is desirable it is expected that any such lubricant would have a limited life and therefore safe biodegradation to allow re-treatment is desirable. An example of a possible material is poly(lactic acid) (PLA) or derivative, a well known material which is (1) biodegradable (with control over degradation rate by compounding); (2) available/processible as a solid particle, a hollow particle or a hydrogel; (3) available in different forces with controllable hardness; (4) readily accepting other materials attached/grafted or otherwise incorporated.

In one embodiment, the configuration is a central (3-D) core with attached long chain (1-D) hydrophilic molecules. Alternatively, these attached long chain molecules could be lipids, e.g. SAPL's, other PL's or hydrophilic molecules. The material composite core and long chains would have effective particle sizes in the desired range. This is another advantage of PLA in that it can be made into particles of various sizes, for example PLA particles of <0.2 micron have been reported. This combined with the added long chain hydrophilic or lipophilic molecules would allow manufacture of particles in the desired size range.

A lubricant works by reducing friction between bearing surfaces in the knee. The bearing surfaces of greatest interest are the femoral condyles and the tibial plateau/meniscus. The lubricant can function as a thin film (such as when walking) or in a static squeezed flat mode (such as when initiating motion after standing still) certain properties of an optimal lubricant will address each and/or both of these situations. It would not be desirable for any particles present between bearing surface to be harder than the bearing surfaces since this could cause the hard particles to dig into or score the bearing surfaces under load. This would suggest that the particles should be less than the 60 A (shore durometer scale) hardness for healthy cartilage. If used with damaged or degraded cartilage, the material with lower durometers may be indicated.

This lubricant which is composed of (a) particles, (b) long water or lipid trapping chain, and (c) a carrier fluid, saline or preferably or an inert water soluble gel with the viscosity and osmolarity of synovial fluid, will behave as (and in fact is) a non-Newtonian fluid. This will help to address the needs of static and dynamic lubrication in that (i) the particle will help to keep a small separation space between bearing surfaces under static loading; (ii) long chains will trap water or lipids which, in combination with the long chains, will create a lubricity layer for dynamic motion; and (iii) the carrier will assist with injection of the lubricant, and in the case of inflammation, can help restore synovial fluid viscosity.

One aspect of a lubricant is that it functions when in place between load bearing layers. In other words, this is between the femoral condyle and the meniscus and tibial plateau. Herein the improvement of lubrication by pumping lubricant into this portion of the joint has been discussed. It would alternately and/or additionally be desirable to attract, and possibly attach, lubricating molecules/particles to the bearing surfaces of the joint whether natural and/or artificial. It could be desirable to have the bearing surface had an inherent attraction to the particles. This could be accomplished, for example, by having the surfaces and the lubricating molecules/particles being of opposite charge. In the case of an artificial bearing surface a magnetic bearing surface could attract ferrous, or otherwise magnetically susceptible, lubricating. It is possible that these effects could be externally controlled by the application of external magnetic field or be intrinsic properties of the materials. These attractive effects can be used alone or in combination with chemical bonding, for example as described herein applying to SAPL or other PL lubricants.

Figure 14:
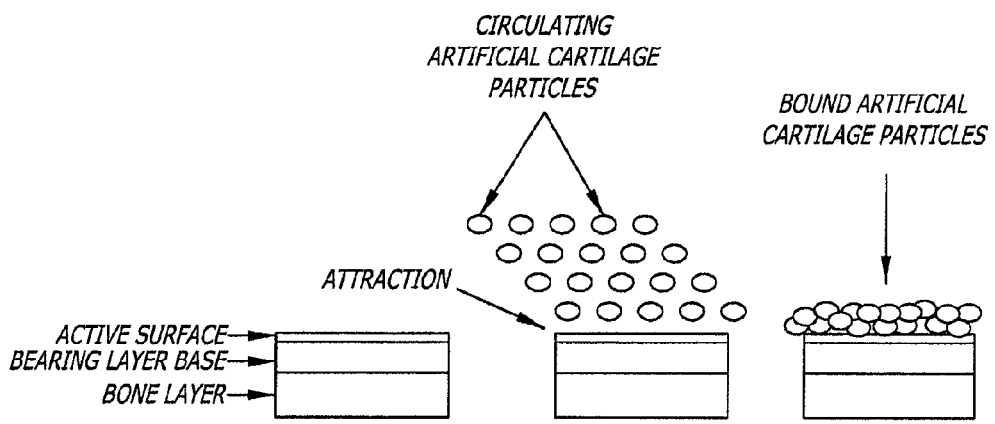
FIG. 14 shows a process of repetitive surface coating on an artificial cartilage.

Similarly, it would be possible to create particles of materials which mimic the properties of the bearing layer itself. This could create a self-healing and/or self lubricating bearing surface where the combination of the loading and tracking of the surfaces and the deposition and entrapment of new material could mimic the living cartilage. Surface coating can be repeated by a repeat application of artificial cartilage or lubricant particles circulating in the SF (as shown in FIG. 14).

Materials for this could include the PLA or PVA hydrogel and other materials, including the particulate lubricant described herein. The PVA, or other hydrogel, could optionally be treated as described herein to create a lipid attracting volume. Particles for this application could be the same size as the lubricant described above or could be larger depending upon the clinical situation. The receptive bearing layer base could be natural cartilage or an artificial material as described herein. Optionally have an increased surface roughness or other treatment to increase the adherence of the particles to the surface. Artificial cartilage materials could mimic the properties of natural cartilage and have, for example, durometer of 30 A-60 A; a SF lubricated static friction of 0.20-0.40 (or 0.10-0.100); and a SF lubricated dynamic friction of 0.03-0.05 (or 0.01-0.010).

This method of replenishing and/or replacing the cartilage could be adjusted to use materials which are liquid when in synovial fluid but then form a gel or hydrogel in-situ. This is a variation on the form in place methodology as it can be used to selectively deposit/create material on a surface from a circulating biocompatible liquid. For example, Chitosan, a polysaccharide which is nontoxic, biocompatible and biodegradable can be formulated to gel at physiologic pH (7.4). Furthermore, Chitosan can be processed to combine with fatty acyl chlorides to form a hydrogel. Carriers can be used to attract the Chitosan to the bearing surfaces or a negatively charges bearing surface base could attract positively charged Chitosan molecules.

Composite Meniscus

The meniscal replacement shown herein is one embodiment of a composite meniscus. Current replacement menisci are homogenous. The basic composite meniscus can have 2, 3, 4 or more layer/components as shown below.

Materials can be selected or optimized for their specific function. The bearing layer should be durable (resist shear forces) and be lubricious. Crosslinked HDPE is one example of a material candidate for this layer. This layer can be further coated to improve its lubricity with a hydrophilic or lipophilic coating, e.g. a SAPL absorbing or adsorptive coating.

FIG. 8 shows a replacement Meniscus, with optional tibial plateau cover. This example of the replacement meniscus is shown including a tibial plateau cover. A soft meniscal portion is molded from a polymer of appropriate durometer. It can be optionally reinforced in a uni, bi or triaxial manner to resist flex and/or prevent tearing or fragmentation. This can be accomplished using fibers and or metal reinforcing bands or wires. This is then optionally attached to a backing plate for mounting and interfacing with the tibial plateau. The replacement meniscus can be attached to the backing plate along all or a portion of its circumference. In certain clinical situations, the "horns" of the meniscus are not bonded to the backing plate to allow flexing during gait. The backing plate can be attached to the tibial plateau using screw type fasteners, adhesives or other means know in the art.

Exemplary prototypes of this configuration have been assembled using a molded 50 A silicone rubber adhesively bonded to a 0.25 mm thick metal backing layer. The area of the tibial cover included a layer of a fiber reinforced lubricious fluoropolymer. Though not included on these particular prototypes, a hydrogel coating for the silicone layer was also available.

The lateral restraint would be to stabilize the knee as it bends and this component would be expected to have been selected for controlled resistance to deflection. High density polyethylene (HDPE) or a fiber reinforced medium density polyethylene (MDPE) are examples of the types of materials which could be used for this application. The cushioning layer would be selected for its ability to deform under load and absorb shocks; a low density polyethylene (LDPE) or PE/EVA blend could be appropriate for this layer.

The mounting layer would be selected for rigidity to facilitate interlocking (e.g., with a dovetail) with the optional separable tibial base (e.g., SS or Ti) and for its ability to be bonded to and integrated with the other components (e.g., HDPE). The mounting layer could also include means such as fiber reinforcement to facilitate attachment, and resist pull out by sutures or other means such as darts or anchors The materials described are all polyethylene, for purposes of illustration. The materials can be thermally bonded together and the bearing layer is the material often used in knee prostheses. Alternate materials may be selected from a variety of sources: biodegradable (e.g., PLA, PVA, PGA, PU and the like), hydrogels or hydrophilic (e.g., PVA hydrogel, polyacrylamide, and the like), scaffold for cell growth (e.g., PU, collagen, and the like) and metals such as porous Tantalum, SS and NiTi or the like. The material can combine the above properties and/or components and/or materials to achieve the desired device useful life and properties.

A Meniscal liner or cartilage prosthesis, e.g. a meniscal or condylar prosthesis, consisting of multiple layers (see FIG. 13A) is illustrated in an exemplary embodiment with three layers as shown here:

1. Backing layer
   a. For mounting to the bone/cartilage surface
      i. (Optionally) to hold the device in place e.g. by ingrowth into a porous surface as described herein
      ii. (Optionally) to allow motion relative to the bone/cartilage surface
      iii. (Optionally) to incorporate barbs, screws, cement or other means to hold the backing layer to the bone/cartilage
      iv. (Optionally) to incorporate reinforcement to facilitate attachment using sutures, darts, anchors et al.
   b. For lateral support (resistance to wrinkling due to lateral forces)
   c. As a "last line of protection" of the bone/cartilage surface
      i. (Optionally) stronger and/or lower wear than the other layers
      ii. May compromise properties which prevent damage to mating surface for increased strength
      iii. Ideally, if exposed by wear of the other surfaces, to function and be lubricious with natural synovial fluid
2. Transition layer
   d. To provide a transition between the backing and sliding layers
      i. Optionally (1) to be of intermediate wear and/or strength; (2) to incorporate a wear indicator; (3) to be formed from a material with mechanical properties identical to the sliding layer; (4) to be formed from the same material as the sliding layer modified/adjusted to have different mechanical properties
   e. To have properties that will induce little or no damage to its mating surface
      i. May compromise properties which prevent damage to mating surface for increased strength
      ii. When exposed by wear of the sliding surface, to function and be lubricious with natural synovial fluid
   f. To provide cushioning
      i. May resist deformation more (or less) than the sliding layer
3. Sliding interface layer
   g. To provide a low wear low friction sliding surface
      i. In the case of the meniscus to allow the femoral condyle to slide
      ii. To function and compatible with natural synovial fluid
      iii. (Optionally) to incorporate a wear indicator
   h. To have properties that will NOT damage its mating surface
      i. To provide cushioning An exemplary combined meniscal-tibial liner is shown in FIG. 7B which applies some of the above-identified specifications.

Figure 16:
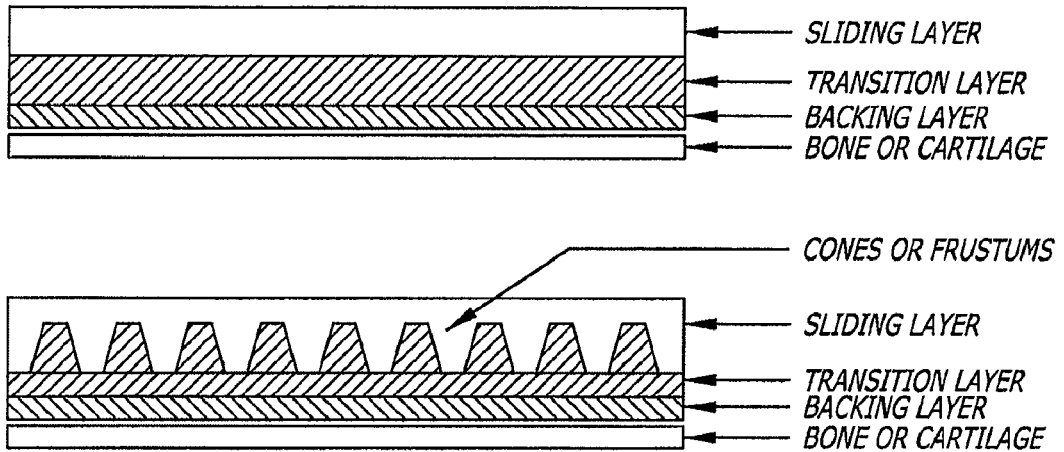
FIG. 16 shows one embodiment of a cone/frustum sliding layer construct.

In the following embodiment, simple layers are shown in FIG. 16.

In the above cone/frustum embodiment the sliding layer can be radiopaque or MRI opaque. With lucent transition and backing layers when the device is viewed from above, and when the opaque layer is worn away, lucent circles become visible or more visible. The location of the circles will indicate the location of the wear while the diameter of the circles will indicate the degree of wear. Wear past the depth of the cones will be visible as a widening non-opaque area. This can alternately or additionally be accomplished by using colorants if wear detection by direct (arthroscopic) vision is desired.

Double sided devices for placement between cartilage surfaces (e.g. one embodiment of a meniscus liner) can be created similarly using, for example, a 5-layer structure: 1. sliding layer; 2. transition layer; 3. backing layer; transition layer; and 5. sliding layer.

In the above exemplary embodiment, the materials for the device could be as follows:

1. Backing layer
   a. Crystalline Polyvinyl Alcohol
2. Transition layer
   a. A PVA hydrogel, slightly stiffer than the PVA-PVP of the sliding layer
3. Sliding layer
   a. PVA-PVP
      i. As described by Katta et al (Bioengineering Conference, 2004. Proceedings of the IEEE 30th Annual Northeast, Publication Date: 17-18 Apr. 2004. pp. 142-143)

ii. Including an MRI-opaque ferromagnetic additive

An exemplary meniscal liner is shown in FIG. 7A which applies some or all of the above-identified specifications.

In another embodiment, the backing layer can be or can mate with a bone interface layer that allows total or partial relative motion of the meniscal layers relative to the bone interface layers. An example of this could be a metal tibial cover with a multilayer meniscus anchored to the tibial cover at its lateral or mid portion while the horns of the meniscal layers are allowed to flex and/or move as the joint extends and flexes. In this case, the metal layer not covered by the semilunar shaped meniscal prosthesis would be covered with a stationary lubricious low wear surface (e.g. a phospholipid coating or a multilayer structure as defined herein). Metal backings can optionally be attached or use ingrowth for anchoring as previously described herein.

In these or other embodiments (and other types of meniscal prostheses or meniscal wafer/liner type devices), as an alternative or in addition to anchoring as described herein, the flexing and deformation of the horns or periphery of a device may be controlled by inclusion of a "C" or "O" shaped collar incorporated in the periphery of the device. These support collars can also provide tension on the device to resist lateral forces. These collars can be metal (e.g. NiTi or SS) or a polymer (e.g. PEEK) or a metal polymer combination.

Figure 17:
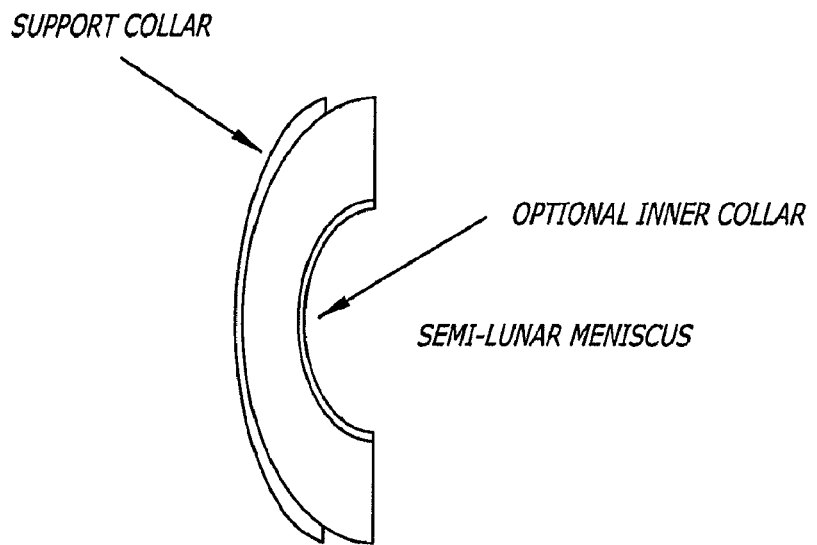
FIG. 17 shows a semi-lunar meniscus having a support collar and an inner collar.

If an inner collar is used (as shown in FIG. 17) it must be configured not to create high spots or stress concentrations when impinged by the mating joint surface (if in the area of joint surface).

Kobayashi and associates reported that artificial meniscus replacement using PVA hydrogel can supplement the meniscus function 2 years after implantation (Biomaterials 2005; 26:3243-3248). Neither wear, dislocation, nor breakage of the PVA hydrogel meniscus implant (90% water content) was observed. They also proposed a composite meniscus of PVA hydrogel and the tissue inducing polymer binding to surrounding peri-meniscus area.

Meniscus Liner Anchoring

Figure 18:
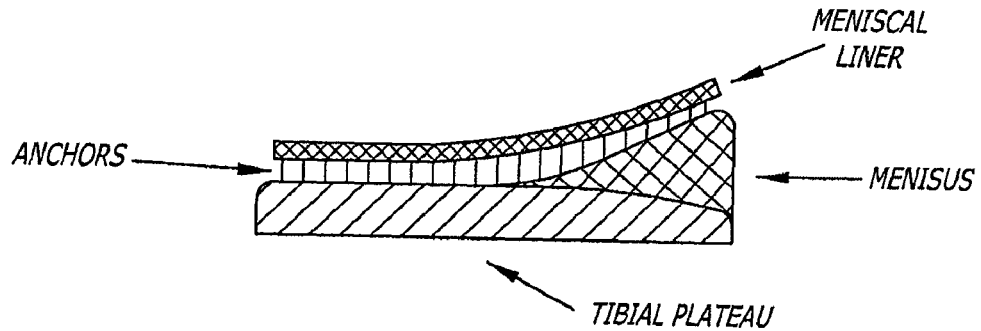
FIG. 18 shows a meniscus liner having prongs or anchors.

An implanted ML will be exposed to both normal (perpendicular to the plane of the ML) and lateral (in the plane of the ML) forces. While normal forces would tend to compress the ML between the femoral condyle and the meniscus/tibial plateau, lateral forces can induce lateral or sliding (or gliding) motion of the ML relative to the meniscus/tibial plateau. Note that in some clinical conditions, the ML is intended to remain stationary relative to the meniscus/tibial plateau while the femoral condyle slides over the surface of the ML. To prevent lateral motion of the ML relative to the meniscus/tibial plateau there are a number of structures which can be employed as follows:

(1) prongs/anchors—Prongs or anchors extending out of the plane of the ML where they can (i) extend into the cartilage/meniscus, (ii) extend through the cartilage into the tibial plateau (TP) as shown in FIG. 18.

Optionally the anchors can be angled to improve their resistance to lateral forces/motion. Forces will be primarily front to back but they can/will also be side to side.

(2) Ingrowth—tissue ingrowth is a well known method for establishing an implant. A porous metal such as sintered Tantalum or a felt type material or other tissue ingrowth material may be secured to the meniscal/TP side of the ML or the ML material itself may be configured to encourage ingrowth, optionally chemical means such as growth factors or autologous blood clot may be used. Optionally the meniscus/TP may be prepared to encourage ingrowth by being pierced/scored or other equivalent means to the point of bleeding to provide clots (blood cells, endothelial growth factors, platelet derived growth factors, other growth factors, and fibrin etc.) and a healing response to encourage ingrowth.

Figure 19:
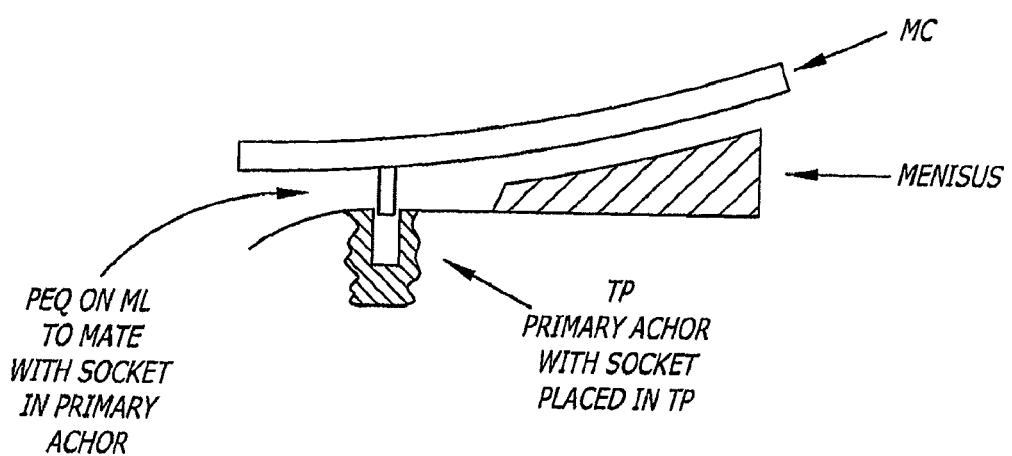
FIG. 19 shows a meniscus liner having screw or nail like anchors.

(3) Screw/Nail/Anchors—In some cases, a 2-stage anchoring process may be desirable. In this case, the meniscus/TP is prepared by the placement of one or more primary anchors to which the ML is thus attached (see FIG. 19). This attachment can be with a peg or socket or other means known in the art.

The primary anchor can screw or by other means be secured in the TP and/or meniscal. Note that forces on the primary anchor will, for the most part, be lateral and front to back in particular, and the anchor should be optimized for resistance to front to back lateral motion. An example of this could be something similar to an arrowhead with blade surrounding a socket. In this case, the broad side of the arrowhead would be oriented to resist front to back motion. Use of individual pegs to resist lateral motion of a meniscal liner can have additional benefits by allowing or (by using a concave or concave shape) encouraging separation between the liner and the underlining tissue. The combination of this separation and the motion/compression due to gait and joint flexion and elongation can effectively improve circulation of synovial fluid by pumping the synovial fluid under the device to the living cartilage.

One aspect of an ML type implant is that it would be subject to wear and may fail mechanically as a result of wear and/or the stresses imposed by normal and/or athletic activities. Since it is likely that an ML would have a finite useful life it is desirable that as the implant nears the end of its life it is not subject to catastrophic failure in the event, it is not removed prior to the end of its useful (undamaged) life. For the purposes of this discussion, we would grade some primary failure modes as follows: device fragmentation (worst), splitting or tearing (bad), or thinning/wearing through (most desirable failure mode).

Cast or extruded polymeric sheets can be prone to fragmentation as a failure mode. This can be reduced by the inclusion of fibers as reinforcement. Fiber reinforcement can be accomplished, for example, by adding chopped fibers, woven strands, or layered strands. Inclusion of chopped fibers in a polymer matrix can reduce and/or delay failure but the failure mode of this type of reinforcement can still be fragmentation. Woven fabric incorporated into and/or coated by a polymer can be the most resistant to fragmentation; however, the over and under nature of the fabric weave can be abrasive once the overlying polymer has worn away. This can be minimized by selecting fibers which are softer than the condyle cartilage which will be sliding over the weave fibers. Layers of parallel fibers will be likely to be weaker than a woven fabric when used in a polymer composite construction as an ML. However, if the top layer of fibers is aligned with the primary motion of the condyle over the TP, exposed fibers will be less likely to abrade the cartilage.

In clinical situations, material selection and the ability to detect the progress of wear of an ML will be factors in determining the appropriate structure/reinforcing of an ML. Further, detection of the wear progression or wear on an implant before failure or before wear becomes detrimental to the patient can be desirable. The defining parameter of an ML is its height or thickness. The thickness of an ML defines the height (or separation) of the knee joints. As the ML wears, it would be expected that the thickness and height would be reduced. Though significant height change can be detected using known imaging techniques (e.g., MRI), greater precision could be desirable. For example, in the case of a fabric reinforced ML, it would be desirable to know when a certain thickness of polymer remained above the fabric. This could be accomplished by creating a layered polymer above the fabric where for example radiopaque and radiolucent layers of 0.5 mm could be alternated. Similarly, ferromagnetic particles could be used to create such a structure that could be visualized using an MRI.

Another alternative would be to have a radiopaque or Ferro-opaque layer 0.5 mm above the fabric in which case the distance between the opaque layer and the bone vs. the known preoperative distance corresponding to the articular cartilage would indicate the wear limit had been reached. Please note that the strategies can be used in many scenarios, in addition to the fabric reinforced polymers. Another approach would be to have a layer or defined zone of the material subject to wear been impregnated with a chemical marker. This chemical marker would be compatible and inert in that it could have no effect on the body means of detection and could be by a routine blood test or other diagnostic means.

One embodiment of this type of detector could be a material such as methylene blue, a well known medical dye. This material has been known to turn urine blue when ingested. If impregnation and wear does not release sufficient material to be detected, then marker material can be deposited in a small pocket or reservoir in the implant which will be released by wear.

One other aspect of an implant relating to wear is the issue of replacement. Removal of an implant can be a problematic part of the replacement procedure. The idea of degrade-on-demand (DOD) is that, when a naturally wearing or degrading implant should be removed, the materials would allow quick and easy replacement by accelerating the wear/degradation by causing the device to rapidly degrade to allow reabsorbance and/or removal (for example, by flushing).

For example, an ML may be constructed of a polymer which is soluble in DMSO at body temperature. When wear is detected, the knee joint may be flushed with DMSO until the ML degrades and is flushed out of the knee joint by the flush fluid (DMSO). This can then allow immediate replacement of the ML. Similarly, anchors used to retain the ML in place may be soluble in DMSO or some other biocompatible solvent. This would facilitate release of the ML from its attachment to speed up or ease removal. Another aspect of degradation on demand could be automatic degradation. This could be an embodiment of a multilayer construction as described herein. In this case, for example, an inner layer made of gelatin or some other rapidly dissolving material would be surrounded and sealed by a water impervious layer which could then be combined with a primary outer layer composed of a hydrogel. The inner layers could provide bulk and/or support to the softer outer layer which will be of low friction and the primary load bearing interface layer. Wear of the device through the water impervious layer would allow water to attack the gelatin layer and a rapid decrease in the size and stiffness of the device. Though this may be a painful means of informing the patient that it is time to remove/replace the device, its removal will be simplified by the dissolution of the inner layer.

Magnetic Unloading and/or Alignment

The knee joints bear the weight of the body and have transient loading more than double the body static weight. The weight translates to normal forces on the bearing surfaces of the joint. Reducing these normal forces can reduce the load, and therefore the wear of the joint. It is suggested herein that opposing magnets placed in or on the femoral condyle and tibial plateau could be used to reduce these normal forces. Since it is desirable for this force reduction to occur during gait and not only when standing, it is preferable that this magnetic opposition occurs while the joint flexes or extends.

The following options include both means to preserve and/or replace the bearing surfaces of the joint. In the case of replacement of the bearing surfaces (e.g., in a total knee replacement) all or part of the femoral and tibial components which are anchored to the bone are typically metal and could include and/or be constructed from or include magnetic materials. For example, rare earth magnets could be used with both components having like poles (e.g., negative) facing each other. If it is desired to unload the joint while preserving the bearing surfaces of the knee, the mechanism as shown in FIG. 20 can be applied.

In this case, the femur has two or more curved magnets which follow the arc of motion of the femoral condyle as it slides along the tibial plateau.

Opposing magnets in the tibia, shown here as opposing pairs, can be straight or curved depending upon clinical requirements. Though the opposing magnets are intended to provide a reduction in the upward normal forces, geometric relationships can be selected to include lateral force vectors to help stabilize the joint.

It is understood that lateral forces can be used to stabilize a joint. These forces can, by their orientation, help to align the path of the elongation and flexion of the knee. Thought the rods should be parallel to each other for proper tracking they can be angled to the left or right from the natural axis of the relative (e.g. femoral vs. tibial) bending of the joint. In certain clinical situations, it may be desirable to change this relative angle. The gentle magnetic bias imposed by these off axis magnets can result in a reorientation of the relative bending angle.

In other clinical situations, it may be desirable to adjust the left-right (inside-outside) angle of the joint. Use of magnets on one (not both) sides of the knee would result in biasing forces which could result in realignment of the side to side tracking of the knee.

Meniscal Allografting

One aspect of the partial meniscectomy, particularly in the case of an acute injury to a young patient, is that the tissue removed is basically healthy. During the partial meniscectomy procedure, the tissue can be collected, prepared and then reimplanted into the meniscus as an allograft. Collection could be performed using an arthroscopic shaver (which will result in relatively small chunks) or other methods can be used to remove the tissue block.

Tissue allograft preparation could consist of one or more of the following: (a) slicing, dicing, grinding, (b) and optionally mixing with other components such as blood/clot, growth factors and/or other agents, (c) preparation for implantation could be as simple as loading in a syringe alternately the tissue could be loaded into a miniature sausage casing (optionally biodegradable). Sausage casing implies porosity with porosity optimized for nutrients and possibly blood cells.

Re-implantation could be as simple as injecting the tissue back into the remaining meniscus as a bulking agent or if loaded in a sausage casing could be all or partially implanted.

Though it is not necessary that the autograft sausage traverse the meniscus from outside-in (or inside-out), this has advantages in that at least a portion of the autograft is exposed to the vascularized meniscal rim. Therefore, the autograft itself may serve as a conduit for nutrients et al. from the outer rim to the inside portions of the meniscus.

The exposed portion of the autograft may be protected by an ML as an option. Similarly, multiple autografts may be used to form a replacement for the tissue removed. Also additional autogenous material may be added to the meniscal tissue to enable use of a larger number of autograft plugs.

Other Aspect-Custom Condyle Caps

The custom condyle cap (CCC) is based upon the concept of covering the existing surface(s) at the femoral condyle with a custom made form fitting prosthesis. One example is a half red blood cell shape that covers the condyle to relieve pain. For simplicity, the following examples would model the condyle as a hemisphere. The CCC is a customized anatomic implant. The CCC may be made of a metal, such as NiTi as follows: (a) image the condyle or condyles; (b) create male & female tools; (c) stamp and clamp a sheet of metal between the tools; (d) trim the sheet as appropriate (this step may precede step c above); (e) if integral retainer tabs are included with design, position tabs in their final intended position; (f) heat the metal sheet and tools above the transition temperature (about 1000° F.) to the austenitic phase; (g) after an appropriate time at the desired temperature, remove CCC from tools and cool below the metal austenitic/martinesetic transition temperature of about 90° F. (Note: the metal NiTi is selected to achieve this austenitic/martinestic transition temperature); (h) reform the CCC to be optimal for the desired surgical procedure for implantation/attachment; (i) maintain CCC below the transition temperature until implantation; and (j) implant and allow CCC to achieve its final shape on the face of the femoral condyle. Note that with shape memory CCC's, it is critical that the CCC be maintained at temperature until positioned for attachment to the condyle and maintained in position until shape change is complete. At any stage, generally after (e) or (h), the metal can be coated on one or both sides with an appropriate polymer (e.g. a PE or Fluoropolyment or a hydrogel) or other coating. If applied after (f) or (g) and before (j) it must have sufficient flexibility deformability to accommodate the shape change at step (j). If applied before step (f), the coating must withstand the processing temperature and have the flexibility/deformability previously mentioned. If applied in-situ using attraction deposition as mentioned herein, the metal should be made receptive/attractive to the coating.

Figure 10:
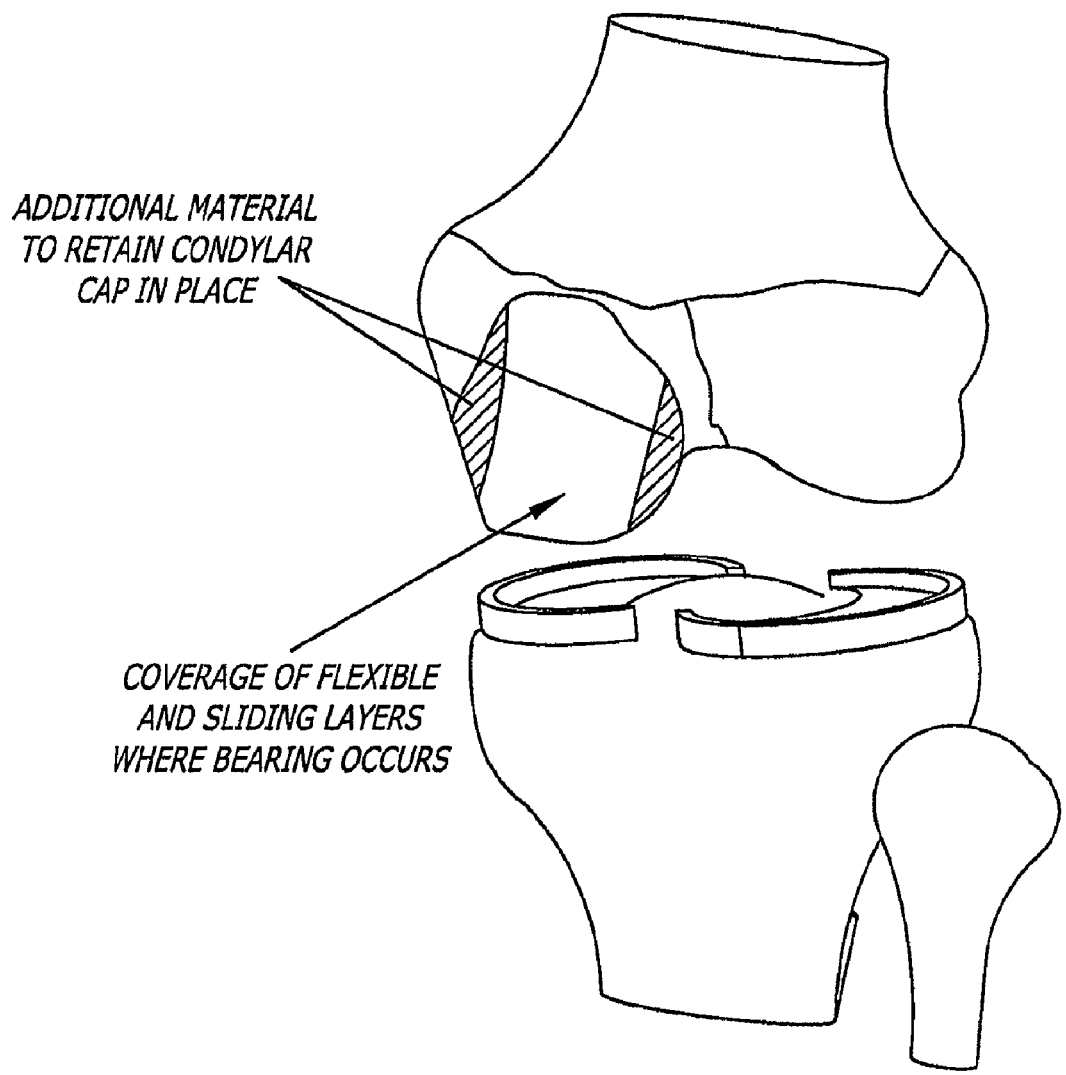
FIG. 10 shows a condylar cover.

FIG. 10 shows a condylar cap with a lubricious bearing surface and surfaces on the side to hold the cap in place. Though this example of the condylar cap is intended to represent a custom anatomically designed specifically fit on this individual patient's anatomy, it could be also a standard implant placed on a prepared surface. In this example, a 3-layer structure is employed with a flexible middle l and a top sliding layers limited to the load bearing regions of the device. The backing layer has additional material which extends around the femoral condyle to retain the device in place. Optionally additional fastenings and/or adhesives can be used to hold the device in place.

Use of a shape change material for a CCC is exemplary. Stainless steel, titanium or other materials (alloy with suitable fabrication techniques) can be used. Materials used for CCC's may have an impact on surgical procedures. Flexible or shape changing implants may allow implantation through a smaller incision or even arthroscopically. NiTi can be used to make a superelastic CCC also. The concept of a custom cap of this invention may apply to other implant caps beyond the standardized shaped and sized condylar caps.

One aspect of the CCC is that it is ideally of a relatively thin thickness or cross-section. Another aspect is that it requires little or no removal of bone. Cartilage overlying the condyle is optionally or non-optionally removed. The CCC designs can include coating and/or layer(s) which would simulate or substitute for the cartilage. This artificial cartilage may be designed to be replaceable. It can be PE, crosslinked PE, hydrogel or other suitable material. This artificial cartilage layer can also optionally include self-healing capability as described above.

In an extremely superelastic CCC, the CCC may be formed and then rolled into a cylinder which can be passed through an arthroscopic portal into the knee. The CCC then would unroll and be positioned accordingly. The procedure/method as outlined should include the step of preparing the condyle or condyles for receiving the CCC implant. CCC design may also include spikes or pegs to attach them to the femur and prevent shifting or slipping. Cement or other adhesives can also be used.

Tibial/meniscal cover devices (for medial or lateral compartment menisci) may be constructed as an artificial cartilage covered metal plate over the tibia/meniscus with wings for attachment. In one embodiment, the backing should be directly over the tibia and include a total meniscus replacement. In another embodiment, the above-identified plate is without wings. If needed, the mounting of the cover device is on or very close to the tibial face, possibly under the meniscus replacement. Similarly, a condyle cover may be consisted of a tin backing plate with wings for attachment to an artificial cartilage sliding surface.

Other Solutions-Localization or Relocalization

One aspect of implants which are custom constructed for existing anatomy is the desire or need to match and/or duplicate the geometry of the joint from which the implant was designed with the geometry of the joint into which the implant is placed. This can be an issue when minimally sized incisions or portals are used to place an implant. Current technology for open total knee replacement and especially mini open procedures makes use of cutting guides to correctly position components of the implant. This is also the practice with partial knee replacements such as uni-component (or uni-knee) prosthesis.

One of the advantages that may be achieved with a custom constructed implant is the minimization or elimination of cutting notches in the bone to position the implant. Absent notches cut in the bone or in a situation where an implant is designed and/or constructed using an anatomy dependent notch which may be defined (but not formed) at a procedure other than the procedure in which the implant is placed, other methods and apparatus are needed.

Some aspects of the invention relate to a method and apparatus involving: (1) using an external frame to position markers on the femur and tibia prior to performing an imaging study; (2) at a later date replacing the frame at the same location on the femur and tibia to match the localization of the initial imaging with the implant procedure. Apparatus of the marking would be matched to the imaging modality, e.g., radiopaque for CAT scan marking must be sufficient to define the location in space—specifically a minimum of 3 points on each bone or 2 lines on each bone.

Marker should be designed so as to facilitate relocation, that is, precise relocation of the frame at the follow up procedure.

Markers would prefer to be biodegradable or removable. This can be accomplished by having an opening in the bottom of the marker into which a hydrogel or barbed removal tool can be placed. In one embodiment, the removal tool is part of the frame used for the second procedure (not the first) so removal at the frame removes the marker.

Three markers can have the advantage of surrounding the limb.

Two line type markers can accept and restrain elongated pines that can allow the use of a guide frame that does not need to surround the limbs. The above shows the most basic frame where it is used only to accurately localize and relocalize the limbs. Additional arms or beams attached to the frame can be used to guide placement of an implant or cutting a notch in a base.

The meniscus bears a great deal of the load which is borne by the knee. Replacement menisci have had mixed result while arthroscopic procedures on the meniscus are effective. In an effort to preserve and supplement the performance of the meniscus, the idea of injecting materials into tissue to augment the appearance or function of tissue is well known. U.S. Pat. No. 6,390,096 is an example of where a needle is used to implant a solid prosthesis into the palate to alter the mechanical response of the palate to air flow. The idea of meniscal augmentation or bulking would involve using a needle system, similar to U.S. Pat. No. 6,390,096 to inject a hydrogel or other polymer into the meniscus.

Based upon the clinical situation, it can be beneficial to use a system with a non-coring type needle as is well known in the art. Similarly, use of a needle with a little or no cutting (like a taper style surgical needle) can be beneficial in some cases. The implant which is placed in the cavity formed by the needle penetrating into the meniscus. Then serves to build up, i.e., expand the volume of the meniscus and thereby provide additional support to the joint. Multiple implants can be inserted and repeat procedures can be performed. Implant material can be optionally biodegradable or bioresorbable.

Implant material can be relatively rigid or soft and springy as would be a hydrogel which will cyclically absorb and expel fluid due to changes in external stress. This would duplicate the performance of natural cartilage. Elastomers such as silicone or polyurethane may also be useful in this application. One advantage of this type of implant is that it maintains the meniscus tissue as the bearing material in contact with cartilage and bone. Optionally, the bulking implant can be a growth encouraging scaffold which would facilitate growth and regeneration of meniscal cells. Optionally, the building implant can be biodegradable.

Fixed or variably curved implantation needles may enable/facilitate implantation around the circumference of a crescent shaped meniscus. For the mechanic, one approach to extending the life of a worn bearing is to replace or resurface the worn bearing surface. This can be accomplished through the use of a replaceable liner or added sleeve placed within an existing liner. In the case of the knee, some have considered the meniscus as a replaceable bearing liner and have contemplated replacing the meniscus (for example, U.S. Pat. No. 6,893,463, entire contents of which are incorporated herein by reference).

The idea of the meniscal liner (ML, also referred to herein as meniscal wafer MW) is more akin to the concept of placing a sleeve within an existing bearing liner. A sleeve type liner placed over the existing meniscus and/or tibial plateau could achieve multiple objectives: (1) It can isolate the meniscus from tear inducing shear stresses; (2) It can provide a fresh smooth lubricious bearing surface; (3) It can optionally add height to the joint by adjusting the thickness at the liner; and (4) It can optionally adjust or modify the shape/configuration of the bearing surface of the joint.

The ML can be constructed in a number of manners. One example would be to make a positive mold of the meniscus from CAT or MRI data. This mold could then be used with standard vacuum form equipment. After forming, the liner could be trimmed and optionally modified, coated and/or otherwise prepared for implantation before sterilization. The liner could be made from many materials (some of the following can be thermoformed: PE, PP, acrylic, PU et al., biodegradable materials such as PLA, PGA etc). The ML can also be used as an adjunct to a meniscal tissue engineering procedure. In this case, the ML is used to provide a bearing surface for the joint while a paste graft, collagen (or other) scaffold or other collagen regenerating procedure is performed. In some cases, an ML made from a biodegradable material would be used for this application. In some cases, an ML made from or coated with a hydrogel material would be used for this application.

The ML can be a totally separate component or can be integrated with the graft/scaffold/collagen. In certain clinical situations, a key of the use of the ML can be that it protects a regenerating meniscus. It should be noted that though described as being specific to the knee, the devices and methods might apply to other joints, such as hip and shoulder.

The meniscal liner can optionally include a liner that covers the tibial plateau in addition to the meniscus. Optionally the ML can be porous to allow passage of synovial fluids. Optionally the ML can be made from a hydro gel and/or lipophilic material where the trapped/absorbed water or lipids could improve the lubricity of the ML surface. A mock up meniscal liner was prepared using 0.5 mm PP and a dental thermoforming machine. The ML was trimmed and removed from a meniscus mold. A plastic knee model was then reassembled with the ML in place. Prototypes were also constructed using hydrogel layers of varying thicknesses on the PP backing layer. In bench-top experiments, the knee articulated appropriately with the polypropylene and PP/Hydrogel ML mock-up sheets in place. The bearing surfaces at the knee include the condyles (their articular cartilage lining), the meniscus and the tibial plateau.

The surfaces can be improved in a number of manners using a number of technologies/techniques that differ from improvement of their lubricating synovial fluid. The surfaces could be improved by: (1) making them smoother and harder (to reduce friction and resist wear and damage); (2) making them more lubricious (to reduce friction); (3) making them softer to avoid damage to the natural surfaces; and (4) making them tougher (to resist tears and other damage). The surface improvement could be accomplished by: (1) attaching a material or lubricant directly to the cartilage using a chemical bond; (2) attaching the material or lubricant directly to the cartilage using a photo activated bond; (3) attaching the material or lubricant to the cartilage using a carrier material; (4) attaching an intermediate material to the cartilage which will scavenge and bond active particles, moieties or ingredient circulating in the synovial fluid; and (5) placing an active particles, moiety/molecule in the synovial fluid where it is absorbed by the cartilage.

Long chain hydrophilic or 3-D hydrogel materials may be other candidates for a lubricious coating material. Coating of interpenetrating and/or crosslinking long chains may serve to protect the area and isolate the meniscus from tear-inducing shear stresses while similar coatings may be optimized for hardness and/or load distribution. In many situations, it would be desirable for these coatings to be porous to some degree to allow nutrients and other active agents from the synovial fluid to penetrate to the cartilage underlying the coating.

One method for surface coating the joints could include steps: removing the synovial fluid (SF), replacing the SF with another fluid, drying the interior of the joint, applying a first agent, applying a second agent, applying activity energy (e.g. light, UV light, RF energy), applying a third agent, rinsing the joint and replacing the SF. One aspect of the invention relates to activated coating active components of the synovial fluid, such as SAPL and the like, onto a joint or onto implantable devices (such as a meniscal liner, meniscal wafer, meniscal collar, composite meniscus, condyle cap, cartilage cap, articular bumper, meniscal bulking agent, and the like). The following prior art is incorporated herein by reference: U.S. Pat. No. 4,722,906 issued on Feb. 2, 1988, U.S. Pat. No. 5,512,320 issued on Apr. 30, 1996, and U.S. Pat. No. 6,077,698 issued on Jun. 20, 2000.

Meniscus augmentation is a subset of the idea of cartilage augmentation (CA). Augmenting or bulking (these terms are used interchangeably) agents can be: (a) rigid, elastomeric, porous; (b) biostable or biodegradable (used interchangeably with the term bioresorbable); (c) coated, impregnated or seeded with cells or bioactive agents; (d) biological materials such as cells (e.g., cartilage cells) from the patient or other sources; or (e) combinations thereof.

The bulking agent can be biocompatible and/or serves as a scaffold for the growth and regeneration of cells/tissue. To scaffold, a material must have a combination of surfaces and voids. The voids should communicate as in an open cell form or a matrix of round pellets. The scaffold could be a combination e.g., particles of open cell foam. Scaffold material should be compatible with the cells which are desired to colonize the scaffold and regenerate the desired tissue. Hydrogels can be used as scaffolds and can act in a manner similar to an open cell foam. In addition to compatibility, it can be desirable in some situations to encourage this colonization and regeneration.

Some aspects of the invention relate to a method of meniscal augmentation comprising administering a meniscal bulking agent to increase a volume of the meniscus, wherein the meniscal bulking agent is preferably administered by injection. In one embodiment, the injection step is applied using imaging guidance or arthroscopically under direct viewing. In one embodiment, the meniscal bulking agent comprises a biodegradable hydrogel. In another embodiment, the meniscal bulking agent comprises a crosslinkable hydrogel with a first molecular weight, the crosslinked hydrogel having a second molecular weight higher than the first molecular weight. In still another embodiment, the meniscal bulking agent is a liquid with a first viscosity index before an administering step, the meniscal bulking agent having a second viscosity index after the administering step, wherein the second viscosity index is higher than the first viscosity index. In a further embodiment, the bulking agent has a first volume before an administering step and expands to a second volume after the administering step. In a preferred embodiment, the bulking agent further comprises a scaffold seeded with autologous cells, mesenchymal stem cells or regenerative cells.

This can be done with coatings, impregnation and/or preceeding the material with cells of the desired type. Alternately, some materials (e.g., collagen and PU) inherently or through additives as other types of surface treatment encourage colonization and cell growth. One exemplary CA agent could be a biodegradable foam that would act as a scaffold. This material could be injected into the cartilage as a liquid and form the foam in-situ as described in U.S. Application publication No. 2001/0043913 A1. Alternately, small pieces of foam material can be passed through a cannula to the implant site. Examples of this could be foams formed from PU, PLA, PGA or other materials commonly used to make biodegradable structures. Foam particles could also be made from a hydrogel. An example of material to be added to or incorporated into a CA agent to encourage cell growth and regeneration could be growth factors or allograft cells such as described in Arthroscopy 2006; 22(3):291-299.

The combination of the foam scaffold which has been designed and/or selected to provide mechanical support of the cartilage before it degrades and while the cells infiltrate the scaffold and regeneration.

Cartilage Augmentation Methods: One of the aspects of tissue augmentation is matching the augmenting material to the tissue/anatomy being augmented. Specifically soft tissues are augmented by relatively soft materials and hard tissues. Different tissues also require different methods for implantation. Soft tissues allow material to be injected directly into tissue where the injection pressure creates space in the tissue. In the case of hard tissue, means to create space in the tissue must be developed. In one embodiment, a balloon was used to create space in bone to allow implantation of cement in the space created within a vertebrate.

Cartilage, articular and meniscal, are intermediate tissues softer than bone but harder than soft tissue such as muscle. Furthermore, both the meniscus and most articular cartilage (e.g., that overlying the femoral condyle) are attached on one side to bone. In the knee and other joints, one or more of the non-attached surfaces are lubricated bearing surfaces. These cartilaginous tissues also are compressible and serve to cushion loads transmitted within and through the joint. Furthermore, some cartilage, in particular the meniscus, is known to be prone to tearing and other mechanical failure.

These aspects of the function and properties of cartilage suggest that any material/method for CA address one or more of the following issues: (1) do not result in the cartilage detaching from the surface of the bone; (2) do not split or tear the collagen or create stress concentrations; (3) do not adversely impact the surface smoothness or lubricious nature of the bearing surface of the cartilage; (4) do have properties that match the cushioning of the natural materials mechanical augmentation; (5) do have the ability to be implanted in a manner to increase the size/volume of the cartilage—volume augmentation; (6) optionally provide a surface or surfaces to allow cell growth and regeneration—biologic augmentation; (7) optionally accelerate/facilitate biological augmentation by drugs, cell seeding et al.; and (8) do encourage/enable healing and ultimate fusing and re-attachment of the augmented tissue.

The following is an example of a detailed CA procedure. Some Optimal steps and alternatives are included to provide a better understanding of some of the issues involved in CA:

(1) advance a needle into the cartilage along the margin between the cartilage and its underlying bone;

(2) (alternately) slide a trocar cannula over the needle, or optionally remove the cannula after it has dilated the cartilage;

(3a) (alternately) slide a trephine over the needle and spin the trephine to cut into the cartilage and/or the bone; (3b) remove the trephine and optionally collect any cartilage and bone tissue from the trephine; (3c) optionally suction and/or flush around the needle to collect additional tissue; (3d) optionally set aside the collected tissue and optionally remove any excess liquid and optionally mercerize the tissue into a paste;

(4) optionally pass a balloon over the needle and inflate to deflect the cartilage and create space between the cartilage and bone;

(5) select a material for placement in the created space (in this case, we may select particles of open cell foam of PU, PVA et al.);

(6) optionally mix the foam with the previously collected cells;

(7) optionally add growth factors;

(8) insert a thin cannula over the needle;

(9) remove the needle;
(10) insert the foam cell mixture through the cannula into the space created by the balloon; and
(11) insert a plug through the cannula or suture, close the defect in the cartilage.

Certain aspects of this procedure are optimized for cell regeneration as outlined below: (1) The use of the trephine in step 3 in the above paragraph is to collect tissue for this purpose; (2) Sliding the trephine over the needle along the bone/cartilage border (step 3) allows collection of both cartilage and bone cells. Furthermore, this can optionally cut deep into the bone to cause bleeding; (3) The use of a porous foam; (4) In step 4, the foam provides mechanical support to the cartilage and would also flex to cushion loads in addition to facilitate/accelerate the cell growth and regeneration; and (5) The use of a plug or suture to close the defect at the implant site is to prevent escape of the material from the implant site. As the materials are expected to be pressurized as the cartilage deflects, this step improves the augmentation by providing escape of the cells or the augmenting foam.

Biomaterials for Meniscal Liner

Biomaterials for implantable knee devices, wafer, liner, meniscal/tibial cover, condylar cover may include:
(1) Core material:
(a) High Modulus (>300,000 psi)
Metals—ferrous/non-ferrous metals, metal alloys (stainless steels, cobalt steels, cobalt chromium alloys, Nitinol)
Ceramics—zirconium
Polymers—polysulfones, polycarbonates, polyesters, epoxies, PEEK, polyimides
(b) Moderate Modulus (50,000-300,000 psi)
Polymers—nylons, polyurethanes, polypropylenes, polyethylenes, polyesters, polyureas, polyacrylates, polyvinyl alcohol, polymer blends, natural polymers (collagen)
(2) Optional Reinforcement: (woven or non-woven)
Polyester fibers
Carbon fibers
(3) Optional Lubricious Surface Coating:
Hydrogels—polyacrylates, PVP, PEO
Lipids—phospholipids (phosphatidyl choline)
Protein—tribonectins, glycoproteins There are many biocompatible polymers, such as PVA, polyurethanes, polyolefins, that can meet requirements for the core of the device, (e.g. shore hardness of 70 A to 60 D, or a compressive modulus about 400 kPa). It is noted that the materials challenge is in the wear/friction surface against the natural tissues. Without causing tissue degradation, the device must stand up to the repeated frictional forces in the knee joint, and give acceptable wear with minimal particulate generation. A tough, wear resistant, lubricious surface is needed.

HA Microparticles

The goals for treatment of osteoarthritis using hyaluronate compositions, hyaluronic acid and hyaluronates (collectively herein called as "HA"), can be met by injection of a suspension of HA microparticles into the joint space. The particles will act as depots for supply of soluble HA's in the joint space—a slow or time release of HA's. Suspensions have viscosities similar to that of the carrier fluid, such as saline, therefore injection of large loading doses of HA's are possible. Injection needle can be e.g. 18-22 ga.

Microparticles can be made by known techniques such as spray evaporation, precipitation, emulsification and filtration, or grinding. Particle size needs to be >10µ, preferably >25µ to minimize inflammation and diffusive leaching. A preferred range is 50-1000µ. In some clinical situations, this preferred range could be 100-200µ. High molecular weight of the HA is preferred and MW should be at least 500,000. In some clinical situations MW>1,000,000 or even >10,000,000 may be indicated. Bacterial sourced HA may be preferred to minimize pathogenic contamination and allergic reactions. Since the HA particle is soluble, it will initially become hydrated and soft, thereby further acting as a cushioning agent within the joint space.

HA particles can form in-situ from a liquid injection. Methods for self agglutination of this type have been described by Bell et al. Alternately, HA can be bound or otherwise attached to a molecule which will aggregate into particles in situ.

Water soluble radiopaque agents (RO) such as metrizamide may be added to the composition to allow visualization upon injection to insure the target joint space is successfully treated. RO ingredient could alternately be biodegradable and/or MRI visible. MRI visible agents can be, for example ferromagnetic. RO ingredients, such as gadolinium complexes, could alternately enhance MRI visibility. RO agents can be optionally incorporated in particles and/or bound to HA molecules. RO agents can optionally be excretable through the kidneys such as diatrizoate meglumine Dissolution rates can be adjusted. Rates can be decreased with larger particle sizes or incorporation of additives to retard dissolution, such as lactic and/or glycolic acid polymers, PEG, collagen, gelatin, etc. Use of the free HA acid or the partial salt of HA (sodium, calcium, ferric) or cross-linking may also decrease dissolution times. Other methods e.g. cross-linking can also be used to control the dissolution of HA. Cross-linking is an example of a method that is known to effect the hardness (durometer) and durability of materials. Cross-linking can be induced, for example, chemically or by radiation.

HA can be formed into particles of various durometer hardnesses. In most clinical situations it will be desirable that the HA particles be softer (with lower durometer numbers) than the cartilage to avoid damaging the cartilage. Bae et al. have published data indicating the durometer of young healthy cartilage can be on the order of 60 Shore A while the durometer of older or unhealthy cartilage can be on the order of 30 Shore A. The preferred durometer of the HA particles would range from 10 Shore A to 50 Shore A depending upon the clinical situation. This invention also includes a method by which the durometer of the cartilage will be measured, and a HA particle durometer selected based upon the durometer of the cartilage.

Therapeutic medications, such as steroids, growth factors, etc., can also be incorporated into the HA particle. Lubrication enhancers, such as proteins, e.g. lubricin or phospholipids, e.g. dipalmitoyl phosphatidylcholine may also be incorporated in the formulation. For example, Pasquali-Ranchetti et al. have described methods by which HA and PL's can be combined.

Alternate Embodiments

Another approach is to inject and form a large depot of HA within a space in the joint capsule (bursa), similar to slow release (3 to 6 month) drug delivery depots such as Depot Provera and Lupron Depot. The HA would be formulated with a slow dissolving agent, such as a PEG or a copolymer of lactic and glycolic acids, and injected into a joint cavity to form an in situ depot for HA.

An approach to provide for a greater concentration of HA per injection is to employ a biocompatible co-solvent in the normally aqueous (saline) HA solution for injection. The co-solvent, such as DMSO, ethanol, ethyl lactate, is a "poor" solvent for the HA. Therefore, the solution viscosity with the co-solvent will be substantially reduced from that of an aqueous solution. This will permit a significantly greater concentration of HA for a given viscosity.

A two part product may be manufactured, which consists of the HA/polymer microparticles in a vial (part A) and a second vial containing the liquid vehicle (part B). The liquid from vial A would be injected into the powder in vial B to produce the suspension, and then the suspension injected into the patient. The product could be a dual chamber syringe, with the dry or lyophilized HA/polymer microparticle in one chamber and the liquid vehicle, such as phosphate buffered saline, in the second chamber. The two chambers are mixed to create the suspension immediately before injection. Alternately, the lyophilized HA can reconstitute in situ after being injected as a powder or injected after being pelletized (e.g. compressed) into particles.

Some aspects of the invention relate a method for treatment of osteoarthritis of a patient, the method comprising injecting a suspension of HA microparticles into a joint space of the patient, wherein the microparticles have a hardness number less than the hardness number of a cartilage within the joint space. In one embodiment, the HA nanoparticles are suspended in aqueous solution. In another embodiment, the HA nanoparticles are suspended in a co-solvent that is a poor solvent for the nanoparticles so that the HA component inside nanoparticles are controllably released from the nanoparticles after being injected. In an alternate embodiment, the microparticles comprise lyophilized HA, the lyophilized HA reconstitutes in situ after being injected into the joint space.

An alternate approach would be to use the tissue within the joint as the depot for slow release of the HA. It is known that the cartilage can absorb HA. It is also known that absorption is an equilibrium phenomenon. Typically, 1% HA is injected into joints while 3% HA has been injected in toxicity studies. For example, injecting HA at 3% and maintaining this high concentration of HA until equilibrium is achieved would turn the cartilage into a depot containing 3% HA that could then leach out over time.

Dosages for Slow Release Microparticle Hyaluronates (HA)

Available HA viscosupplementation products (10 to 15 mg HA/ml) provide 20 to 30 mg of HA (sodium salt) per injection, using 2.0 to 2.5 ml per injection. A total of 3 to 5 injections are given once per week. Present average dosage of four commercially available HA products over a course of treatment is 101 mg HA over 4.25 weeks.

Synovial fluid volume in a typical knee joint is 3.0 to 3.5 ml. HA concentration in normal joint synovial fluid is 3 to 4 mg HA/ml. The half-life of HA in the joint space is reported to be about 20 hours with "complete" elimination from the joint by about 4 days.

For an equivalent dosage of a single injection of microparticles, inject 100 mg of HA in the form of slow release microparticles in a suitable carrier, i.e. saline or phosphate buffered saline. The HA should completely dissolve by the end of week four.

For extended therapy, proportionately more HA can be injected that possess longer dissolution times, e.g. 300 mg HA that dissolves within twelve weeks.

Alternatively, more aggressive therapy can be administered by increasing the amount of HA that is injected within a fixed dissolution time, e.g. 300 mg HA that dissolves within four weeks.

Note that dosage regimens with current soluble HA injections are restricted, due to high solution viscosity limitations, and synovial fluid concentration spikes upon each new injection. These disadvantages are overcome with the use of slow release microparticles. In one embodiment, the various microparticles may have distinct biodegradation rates over a duration of biodegradation to 3 months or longer. In another embodiment, the HA-containing microparticles comprise at least two distinct subgroups of microparticles, the first subgroup has its average biodegradation rate that is different from that of the second subgroup.

TABLE 1

Volumes and Weights for a Single Injection of HA Microparticles
The ingredients are:

|  | A | B | C |
|---|---|---|---|
| HA (sodium salt) | 100 | 100 | 100 mg |
| Polymer (control release) | 0 | 100 | 200 mg |
| Particles weight | 100 | 200 | 300 mg |
| Saline (phosphate buffer) | to 2.0 | to 2.0 | to 2.0 ml |
| Particles volume | 0.125 | 0.174 | 0.236 ml |
| Number particles | 240,000 | 333,000 | 452,000 |

Assuming a density of about 0.8 g/ml for the HA and about 1.5 g/ml for the polymer (poly(lactic-glycolic acid)), the densities for the solid microparticles would be 0.8 for composition A, 1.15 for composition B and 1.27 for composition C. (Density may be decreased somewhat due to the production method for the microparticle.)

Since density is equal to g/ml, the volume that the microparticles occupy would be 0.125 ml for composition A, 0.174 ml for composition B, and 0.236 ml for composition C. Particle size has no significant effect on total volume of the suspension. By calculation, each 100 µm microparticle sphere occupies $0.522 \times 10^{-6}$ cc.

The amount (if any) of the polymer for control release depends on solubility of the HA (sodium salt or free acid), HA particle size, and how it was made, as well as the selection of the control release polymer. For example, polyglycolic acid dissolves in vivo over a period of weeks; polylactic acid dissolves over several months.

There is a limit on how much solids can be injected in 2.0 ml of fluid, probably about 400 mg. An injection volume of 2.5 ml could hold up to 500 mg.

Hydrated particle hardness will also depend on selection of the HA and polymeric ingredients.

Joint toxicity due to the presence of microparticles may be addressed by injection of the microparticle depot into a "safe" joint space, such as bursa.

Subcutaneous Depot

Implant HA in a manner similar to a subcutaneous bleb or where the injected agent (liquid and/or solid) is injected directly into tissue where it creates space rather than into an existing space or potential space as a slow release subcutaneous depot to increase concentrations.

Use of the suprapatellar fat pads as a location for an injected intracutaneous depot. Just above the patella and right behind the quadriceps tendon is the anterior suprapatellar fat pad. Just anterior to the femur is the prefemoral fat pad. Unlike the anterior suprapatellar fat pad, which is relatively constant in shape and size, this fat pad is quite variable in size, and may appear either fairly flat or quite plump. Extending up between these two fat pads is the suprapatellar bursa, an extension of the knee joint space.

The Suprapatellar Bursa as a Depot

These two fat pads can usually be seen on a lateral plain film. Usually the suprapatellar bursa is only a potential space, and contains very little fluid. In this case, the two fat pads are separated by less than 5 mm. If a suprapatellar effusion is present, the two fat pads are pushed apart by the effusion. If the distance separating them is 5 mm or greater, we consider this sufficient evidence to diagnose a knee effusion on plain film The bursa could be the location of an injectable depot. With a 5-10 mm depth, a length of 30-40 mm and a width of 20-30 mm the volume of such a depot could be 3-12 cc.

Refillable Reservoir or Depot

As known in the art, both reservoir and contents distribution and distribution rate control the HA release. Optionally with a port that is local (e.g. on reservoir) or remote (e.g. with a fill tube connecting to the reservoir). Optionally, the reservoir can be expandable and be delivered through a relatively small diameter cannula (e.g. a silicone structure similar to the balloon described in U.S. Pat. No. 4,213,461 which can inflate to many times (e.g. 8-10×) their formed diameter.

Injectable Depot Formula

As an alternative to microparticle injection for depot viscosupplementation, a biocompatible, liquid polymer solution containing the viscosupplementation agent can be injected. Upon injection, the solution immediately solidifies in situ to form a solid mass depot, which dissipates over an extended period of time to deliver the viscosupplementation agent. The biocompatible mass would be about 2 cc, porous and spongy; deliver about 100-300 mg of HA by dissolution/degradation in about 4-12 weeks.

Compositions:
1. Agent—HA: sodium salt, partial salt or other cation, 1 MM+molecular weight
2. Solvent—biocompatible, water soluble: DMSO, ethyl lactate, EtOH/water, acetone/water
3. Polymeric Encapsulant—soluble in solvent, insoluble in water/tissues to form suitable precipitate; biocompatible itself and its degradation products; dissolves/degrades within 4-12 weeks: PLGA, PLA, PGA, PEG, PCL, copolymers, terpolymers and mixtures of the preceding, PHB, PHBV, zein. Optimum concentrations of the ingredients, mole ratios and molecular weights (2-10 k-Daltons) of the polymer to be determined.

PLGA is soluble in DMSO and will form a precipitate depot for proteins (J. Control. Release, (1995) Vol. 33, no. 1, p 189-195). A composition consisting of PLGA with HA in DMSO may work as an injectable depot for HA viscosupplementation.

Viscosupplementation with HA Microparticles Supplemental Information

1. Slow or controlled release of substances, such as drugs, from soluble/degradable microparticle depots has been known and developed since the late 1970's. There exists a well developed technological and patent base. Medical products include: Pharmacia & Upjohn's Depo-Provera (progesterone with PEG, IM injection), TAP's Lupron Depot (leuprolide in PLA microspheres, IM injection), Chiron's Depocyt (cytarabine in liposomes, CSF injection).

2. Results from intra-articular injection of microparticles have been published within the last seven years. These have dealt with site specific release of drugs, such as paclitaxel, hydrocortisone and NTHE's, to treat osteoarthritis. Results have been generally favorable, with claims of biocompatibility of the microparticles within the joint cavity.

Note that small molecule (drug) release is diffusion controlled through the microcapsules, which disappear after the drug is released. We are dealing with a different mechanism in microparticle viscosupplementation, which is particle dissolution or degradation controlled, since we have a macromolecule (HA) to release.

3. The most favored encapsulants are poly(alpha esters), such as PLA, PGA and PLGA copolymers; poly(hydroxyalkanoates), such as PHB and PHBV copolymers; polylactones, such as PCL; and various poly(ethylene glycols). HA has been reported as an encapsulant also.

4. The following patent applications were particularly valuable: U.S. Application publication 2006/0148755 from Genzyme is of special interest—a single 6 ml (vs. 2 ml) injection of HA, good for 6 months; U.S. Application publication 2005/0123593 from J&J describes intra-articular delivery of HA in liposomes (phosphatidylcholine) for extended release of HA; U.S. Application publication 2005/0227911 from SoluBest discloses nanoparticles of starch with HA, forming an inclusion complex, for delivery of HA; U.S. Application publication 2006/0140988 claims compositions and methods for an injectable depot using an emulsion of biodegradable (PLGA) particles for sustained delivery of HA for viscosupplementation, a solvent and surfactant are required.

Exemplary Viscosupplementation Depots e.g. Polymer/Solvent and Compositions of Hyaluronic Acid Polymer/Solvent Compositions: To obtain a composition that models an injectable liquid, which solidifies upon contact with an aqueous environment, it is suggested a process of solidification by precipitation with 8 grams ethylene vinyl alcohol copolymer (Aldrich #414107-100) and 110 grams dimethyl sulfoxide (Aldrich #154938-500); (110 g=100 ml).

The polymer dissolves at room temperature (or ~50° C.) with stirring within a few hours. Store all items in sealed containers, in a dry, cool place.

If a denser precipitate solid is required, use 12 g of copolymer; for a less dense precipitate solid, use 6 g of copolymer. If radio-opacity is needed, add 40 g of tantalum powder (Aldrich #262846-100) to the polymer solution and vigorously shake to disperse the powder.

Hyaluronic Acid Compositions: To obtain a depot for feasibility that will slowly dissolve in vivo and yield hyaluronic acid (HA), it is suggested as follows. This is equivalent to the current treatment, a total of 4 weekly injections—100 mg of HA.

0.1 g HA sodium salt (Sigma or other choice; rooster or bacterial source).
0.3 g poly(ethylene glycol) or PEG (Aldrich #202436-250 rapid dissolution, or #202452-250 slower dissolution in vivo)

One can increase or decrease the amounts of each ingredient during preparation, but keep the ratio of 1:3. Next, try a ratio of 1:10. Mixing can be accomplished by (1) melting the PEG (50-65° C.) and rapidly stirring in the HA, then cool, or (2) mechanically working the two ingredients with a spatula, (addition of few drops of $H_2O$ may help). Remember, HA degrades when exposed to heat and $O_2$. Store all items in sealed containers, in a dry, cool place. Another polymer to try later is poly(lactide-co-glycolide). This will dissolve very, very slowly—weeks to months.

One method of HA administration is to inject a suspension of microparticles. If one wishes, the HA-PEG composition can be cooled (<0° C.) and pulverized, or as a liquid sprayed through an orifice to generate the particles.

Optionally layered particles can be formed (with e.g. increasingly higher concentration HA incorporated into concentric inner layers) thereby maintaining a constant HA dissemination rate.

Long Term Depots

For 2 years at 3.3 mg/day (equivalent to 101 mg over 4.25 weeks)=2×365×3.3=2,409 mg or 2.4 gm 2.4 grams of HA mixed ~50/50 with PGA (or PLA or other appropriate drug carrier) would lead to ~5.0 ml of material+ solvent carrier (e.g. DMSO). With an approximate constant dissolution rate, 3.3 mg carrier/day would dissolve releasing 3.3 mg/day HA. Other carrier/HA ratios and proportional dissolution rates can also be used.

Coaxial depot injection could be used to provide multiple layers such that the outer layers (which will have greater surface area than inner layers) disseminate HA at a slower rate than the internal layers thereby releasing HA at a near constant rate. This could be accomplished e.g. with a constant concentration of HA and a faster dissolving/degrading carrier on the inner layer or an inner layer with a higher HA concentration. Some aspects of the invention relate to a method for treatment of osteoarthritis of a patient, the method comprising injecting a suspension of HA microparticles into a joint space of the patient, wherein the microparticles have a hardness number less than the hardness number of a cartilage within the joint space, wherein the microparticles have plural concentric layers and plural concentric compartments separated by the layers, each compartment being filled with the HA, wherein an outer layer of the concentric layers is configured with a higher degradation rate than a second degradation rate of an inner layer.

Composite Depot

One concern about injectable solvent carrier depots could be related to depot migration as depot size decreases over time. Various means can be combined with an injectable depot to physically contain and/or stabilize the depot over its life as it dissolves/degrades, such as

- Inject into open cell foam where the depot invades and fills the open cells and the struts reinforce the injected material.
- Coaxial injection over a suture or other filament
- Injection into a membrane or other potential space enclosing bladder (porous to fluids and HA or with ports to allow fluid exchange). For example, a thin permeable silicone balloon inflated as the depot material is injected All of the above support materials could be optionally degradable with similar or longer degradation times relative to the depot material.

Depot Anchors

One concern about depots could be related to the potential for depot migration. Depots could be anchors using well known means such as t-tags, sutures, clips or the like. The coaxially injected over suture depot, as well as other depots, could be anchored by barbed sutures. The barbed suture can be especially useful with the injectable depot as a single needle stick can easily anchor and deploy the depot. This can also be accomplished with a t-tag or other type of barbed anchor et al.

From the foregoing, it should now be appreciated that a meniscal implant and other medical devices for treating knee joint has been disclosed. Furthermore, hyaluronate compositions lubricant and methods for treatment of osteoarthritis were also disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method for treatment of osteoarthritis of a patient, the method comprising:

inserting a first magnet on a first side of an implantable meniscus and a second magnet on a second side of said meniscus to create opposing forces; and injecting a suspension of HA microparticles into a joint space of the patient, wherein said microparticles have a hardness number less than the hardness number of a cartilage within said joint space;

wherein said microparticles have plural concentric layers and plural concentric compartments separated by said layers, each compartment being filled with said HA, wherein an outer layer of said concentric layers is configured with a higher degradation rate than a second degradation rate of an inner layer.

2. The method of claim 1, wherein said microparticles comprise lyophilized HA, the lyophilized HA reconstitutes in situ after being injected into said joint space.

3. The method of claim 1, wherein the joint space comprises bursa.

4. The method of claim 1, wherein said nanoparticles further comprise steroids.

5. The method of claim 1, wherein at least one magnet comprises a substantially curved shape.

* * * * *

UNITED STATES PATENT AND TRADEMARK OFFICE
CERTIFICATE OF CORRECTION

PATENT NO. : 8,287,594 B2
APPLICATION NO. : 12/949204
DATED : October 16, 2012
INVENTOR(S) : Cragg et al.

It is certified that error appears in the above-identified patent and that said Letters Patent is hereby corrected as shown below:

In the Drawings:

Sheet 3 of 17 (FIG. 3) at line 4 (approx.), Change "MENSCUS" to --MENISCUS--.
Sheet 6 of 17 (FIG. 6C) at line 4 (approx.), Change "MEISCAL" to --MENISCAL--.
Sheet 7 of 17 (FIG. 7A) at line 3 (approx.), Change "LUBRIOUS" to --LUBRICIOUS--.
Sheet 17 of 17 (FIG. 20) at line 1 (approx.), Change "MENISUS" to --MENISCUS--.

In the Specification:

In column 10 at line 31, Change "Suplaysn," to --Suplasyn,--.
In column 15 at line 43, Change "appropriate," to --appropriate.--.
In column 27 at line 7, Change "and or" to --and/or--.
In column 33 at line 19, Change "martinesetic" to --martensitic--.
In column 33 at line 21, Change "martinestic" to --martensitic--.
In column 40 at line 23, Change "meglumine" to --meglumine.--.
In column 43 at line 5, Change "film" to --film.--.
In column 44 at line 46, Change "vivo)" to --vivo).--.
In column 44 at line 67, Change "gm" to --gm.--.

Signed and Sealed this
Ninth Day of April, 2013

Teresa Stanek Rea
*Acting Director of the United States Patent and Trademark Office*